US012796934B2

(12) United States Patent
Sancey et al.

(10) Patent No.: US 12,796,934 B2
(45) Date of Patent: Nov. 17, 2026

(54) USE OF FLUOROPHORE COMPOUNDS OF THE aza-BODIPY TYPE AS CONTRAST AGENTS IN THE SHORT WAVE INFRARED REGION

(71) Applicants: Universite Grenoble Alpes, Saint-Martin-d'Hères (FR); Universite de Bourgogne, Dijon (FR); Centre National de la Recherche Scientifique, Paris (FR); INSERM - Institut National de la Santé et de la Recherche Médicale, Paris (FR)

(72) Inventors: Lucie Sancey, Villages du Lac de Paladru (FR); Christine Goze, Remilly-sur-Tille (FR); Ewen Bodio, Saint-Apollinaire (FR); Benoît Busser, Le Sappey-en-Chartreuse (FR); Jacques Pliquett, Berlin (DE); Amélie Godard, Dijon (FR); Ghadir Kalot, Saint-Martin-d'Heres (FR); Véronique Josserand, La Tronche (FR); Xavier Le Guével, Grenoble (FR); Jean-Luc Coll, Le Sappey-en-Chartreuse (FR); Franck Denat, Quetigny (FR)

(73) Assignees: Universite Grenoble Alpes, Saint-Martin-d'Heres (FR); Universite de Bourgogne, Dijon (FR); Centre National de la Recherche Scientifique, Paris (FR); INSERM—Institut National de la Santé et de la Recherche Médicale, Paris (FR)

( * ) Notice: Subject to any disclaimer, the term of this patent is extended or adjusted under 35 U.S.C. 154(b) by 1320 days.

(21) Appl. No.: 17/633,610

(22) PCT Filed: Aug. 4, 2020

(86) PCT No.: PCT/EP2020/071865
§ 371 (c)(1),
(2) Date: Feb. 8, 2022

(87) PCT Pub. No.: WO2021/023731
PCT Pub. Date: Feb. 11, 2021

(65) Prior Publication Data

US 2022/0322945 A1 Oct. 13, 2022

(30) Foreign Application Priority Data

Aug. 8, 2019 (EP) .................................... 19315089

(51) Int. Cl.

| | |
|---|---|
| ***A61B 5/00*** | (2006.01) |
| ***C09B 55/00*** | (2006.01) |
| ***C09B 69/00*** | (2006.01) |
| ***C09K 11/06*** | (2006.01) |
| ***G01N 33/533*** | (2006.01) |

(52) U.S. Cl.
CPC .......... *A61B 5/0071* (2013.01); *C09B 55/009* (2013.01); *C09B 69/00* (2013.01); *C09K 11/06* (2013.01); *A61B 5/6869* (2013.01); *A61B 5/6885* (2013.01); *G01N 33/533* (2013.01)

(58) Field of Classification Search
CPC ... A61B 5/0071; A61B 5/6869; A61B 5/6885; A61B 5/349; A61B 5/6846; A61B 5/6847; A61B 5/6886; A61B 5/7271; C09B 55/009; C09B 69/00; C09K 11/06; C09K 2211/107; G01N 33/533; G01N 21/6428; A61K 49/0021; A61K 49/0052; A61K 49/0054; A61K 49/0056; A61K 49/0058
See application file for complete search history.

(56) References Cited

U.S. PATENT DOCUMENTS

| | | | | |
|---|---|---|---|---|
| 7,897,786 B2 * | 3/2011 | Ulrich ....................... | C07F 5/02 548/405 |
| 2015/0291628 A1 | 10/2015 | Danaboyina et al. | |

FOREIGN PATENT DOCUMENTS

| | | |
|---|---|---|
| CN | 108795088 A | 11/2018 |
| CN | 109232621 A | 1/2019 |

OTHER PUBLICATIONS

Bai et al, Chem. Commun., vol. 55, pp. 10920-10923 (Year: 2019).*
Godard et al., "NIR-II Aza-BODIPY Dyes Bioconjugated to Monoclonal Antibody Trastuzumab for Selective Imaging of HER2-Positive Ovarian Cancer", J. Med. Chem., vol. 66, 2023, pp. 5185-5195.
Godard et al., "Water-Soluble Aza-BODIPYs: Biocompatible Organic Dyes for High Contrast In Vivo NIR-II Imaging", Bioconjugate Chem., vol. 31, 2020, pp. 1088-1092.
Bruns et al., "Next-generation in vivo optical imaging with short-wave infrared quantum dots", Nat Biomed Eng, 2017, 1;0056:1-11.
(Continued)

*Primary Examiner* — D. L. Jones
(74) *Attorney, Agent, or Firm* — ArentFox Schiff LLP

(57) ABSTRACT

The present invention relates to the use of an aza-BODIPY fluorophore compound as a contrast agent in the optical window ranging from 1000 to 1700 nm. The invention also relates to the use, as a contrast agent, of a composition comprising said fluorophore compound and a pharmaceutically acceptable excipient and/or a solvent, in a kit comprising an injection system and said fluorophore or said composition, and also to a method for identifying a biological target (such as a healthy or tumour cell, a protein, DNA, RNA, for example).

19 Claims, 2 Drawing Sheets

Specification includes a Sequence Listing.

(56) References Cited

OTHER PUBLICATIONS

Carr et al., "Shortwave infrared fluorescence imaging with the clinically approved near-infrared dye indocyanine green", Proc Natl Acad Sci U.S.A., 2018, 115(17):4465-4470.
Thimsen et al., "Shortwave-infrared (SWIR) emitters for biological imaging: a review of challenges and opportunities", Nanophotonics, 2017, 6(5):1043-1054.
Moss, "Basic terminology of stereochemistry (IUPAC Recommendations 1996)", Pure & Appl. Chem., 1996, 68(12):2193-2222.
Gravier et al., "FRET Imaging Approaches for in Vitro and in Vivo Characterization of Synthetic Lipid Nanoparticles", Mol Pharm, 2014, 11:3133-3144.
Hirsjärvi et al., "Influence of size, surface coating and fine chemical composition on the in vitro reactivity and in vivo biodistribution of lipid nanocapsules versus lipid nanoemulsions in cancer models", Nanomedicine, 2013, 9:375-387.
Garcia et al., "A versatile method for the selective corecrosslinking of hyaluronic acid nanogels via ketone-hydrazide chemistry: from chemical characterization to in vivo biodistribution", Biomater Sci., 2018, 6:1754-1763.
Reagan-Shaw et al., "Dose translation from animal to human studies revisited", The FASEB Journal • Life Sciences Forum, 2007, 22:659-661.
Loudet et al: "Functionalized BF"2 chelated azadipyrromethene dyes", Tetrahedron, Elsevier Science Publishers, Amsterdam, NL, vol. 64, No. 17, Feb. 3, 2008 (Feb. 3, 2008), pp. 3642-3654.
Jiangwei Tian et al: "A pH-activatable and aniline-substituted photosensitizer for near-infrared cancer theranostics", Chemical Science, vol. 6, No. 10, Jan. 1, 2015 (Jan. 1, 2015), pp. 5969-5977.
Qianyun Tang et al: "pH-Tri ggered and Enhanced Simultaneous Photodynamic and Photothermal Therapy Guided by Photoacoustic and Photothermal Imaging", Chemistry of Materials, vol. 29, No. 12, Jun. 27, 2017 (Jun. 27, 2017), pp. 5216-5224.
Nagappanpillai Adarsh et al: "Unveiling NIR Aza-Boron-Dipyrromethene (BODIPY) Dyes as Raman Probes: Surface-Enhanced Raman Scattering (SERS)-Guided Selective Detection and Imaging of Human Cancer Cells", Chemistry—A European Journal, vol. 23, No. 57, Oct. 12, 2017 (Oct. 12, 2017), pp. 14286-14291.
Lijuan Jiao et al: "Accessing Near-Infrared-Absorbing BF 2-Azadipyrromethenes via a Push-Pull Effect", Journal of Organic Chemistry, vol. 79, No. 4, Feb. 6, 2014 (Feb. 6, 2014), pp. 1830-1835.
International Search Report and Written opinion for PCT Application No. PCT/EP2020/071865, mailed Oct. 15, 2020.
European Search Report for Application No. 19315089.3 mailed Feb. 6, 2020.
Ghadir Kalot, et al. "Lipoprotein interactions with water-soluble NIR-II emitting aza-BODIPYs boost the fluorescence signal and favor selective tumor targeting". Biomater. Sci., 2022, 10, 6315.
Elisa Chazeau, et al. "Comparison of the In Vitro and In Vivo Behavior of a Series of NIR-II-Emitting Aza-BODIPYs Containing Different Water-Solubilizing Groups and Their Trastuzumab Antibody Conjugates". J. Med. Chem. 2024, 67, 3679-3691.
Simon Coninx, et al. "Tailored hyaluronic acid-based nanogels as theranostic boron delivery systems for boron neutron cancer therapy" International Journal of Pharmaceutics: X 4 (2022) 100134.
Elisa Chazeau, et al. "NIR-II aza-BODIPY Platform for the Development of a Fluorescent Antibody Drug Conjugate Elisa Chazeau, Angelique Pipier, K. David" J. Med. Chem. 2025, 68, 7232S7242.
Ghadir Kalot, et al. "Aza-BODIPY: A New Vector for Enhanced Theranostic Boron Neutron Capture Therapy Applications" Cells 2020, 9, 1953.
Malorie Privat, et al. "Development of an Immuno-SPECT/Fluorescent Bimodal Tracer Targeting Human or Murine PD-L1 on Preclinical Models" J. Med. Chem. 2024, 67, 2188-2201.
Malorie Privat, et al. "First Comparison Study of the In Vitro and In Vivo Properties of a Randomly and Site-Specifically Conjugated SPECT/NIRF Monomolecular Multimodal Imaging Probe (MOMIP) Based on an aza-BODIPY Fluorophore" Bioconjugate Chem. 2023, 34, 621-628.
Malorie Privat, et al. "Development of an Easily Bioconjugatable Water-Soluble Single-Photon Emission-Computed Tomography/Optical Imaging Bimodal Imaging Probe Based on the aza-BODIPY Fluorophore" J. Med. Chem. 2021, 64, 11063-11073.
Ewen Bodio, et al. "Development of BODIPYS and aza-BODIPYs for molecular imaging applications: from the in vitro to the in vivo" Advances in Inorganic Chemistry. vol. 78, 2021, pp. 65-107.
Wassima Tajani, et al. Near-infrared emitting aza-BODIPY flurophones, impact of N, N-dialkylamino groups on the photophysical properties: systhesis, characterization, and computational studies. Dyes and Pigments 239 (2025) 112773.
Ewen Bodio, et al. Roadmap of Development of Trackable Anticancer Agents Based on Metal Complexes "Strategies and Perspectives for Precision Oncology and theranostics" Advances in Inorganic Chemistry. vol. 86, 2025, pp. 155-186.
Océane Florès, et al. "Aza-BODIPY Platform: Toward an Efficient Water-Soluble Bimodal Imaging Probe for MRI and Near-Infrared Fluorescence" Inorg. Chem. 2020, 59, 1306-1314.

* cited by examiner

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(5)
<223> OTHER INFORMATION: /note="CYCLIC"
<220> FEATURE:
<221> NAME/KEY: MISC_FEATURE
<222> LOCATION: (1)..(5)
<223> OTHER INFORMATION: /note="dF"

<400> SEQUENCE: 1

Arg Gly Asp Phe Lys
1               5
```

-continued

```
<210> SEQ ID NO 2
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2

Ala Thr Trp Lys Pro Pro Arg
1               5
```

USE OF FLUOROPHORE COMPOUNDS OF THE aza-BODIPY TYPE AS CONTRAST AGENTS IN THE SHORT WAVE INFRARED REGION

CROSS-REFERENCE TO RELATED APPLICATIONS

This application is a National Phase of PCT/EP2020/071865 filed on Aug. 4, 2020, which claims priority to EP Application Serial No. 19315089.3 filed on Aug. 8, 2019, the disclosures of which are hereby incorporated by reference in their entireties.

The sequence listing of the present application is submitted electronically as an ASCII file named "044468.00001 Sequence-Listing.txt", created on Jul. 20, 2026, and having a size of 714 bytes. This sequence listing submitted electronically is an integral part of the specification and is incorporated herein by reference in its entirety.

TECHNICAL FIELD

The present invention belongs to the technical field of optical imaging and to the field of contrast agents, and more particularly to the field of organic contrast agents capable of emitting in the wavelength range 1000-1700 nm, corresponding to the very far infrared.

The present invention relates to the use as contrast agent, in the optical window from 1000 to 1700 nm, of an aza-BODIPY fluorophore compound. The invention also relates to the use as contrast agent of a composition comprising said fluorophore compound and a pharmaceutically acceptable excipient and/or solvent, in a kit comprising an injection system and said fluorophore or said composition and also to a method of in vitro or in vivo identification of a biological target (such as a healthy or tumour cell, a protein, DNA, RNA, a lipid, or any other animal or plant biological target part).

In the description, references in square brackets ([ ]) refer to the list of references at the end of the examples.

STATE OF THE ART

Optical imaging is experiencing a new boom with the arrival of high-sensitivity cameras in the detection range of 900 to 1700 nm, range which corresponds to the very far infrared called NIR II or SWIR (Short Wave Infrared). This detection range is particularly interesting in optical imaging as it theoretically allows the observation of fluorescence signals located deeper in the tissue (compared to NIR I imaging), and/or with greater resolution and sensitivity. These observations, described in the articles by Bruns et al, Carr et al and Thimsen et al [1], are possible because of the lower auto-fluorescence of tissues in this optical range.

Below 1000 nm, many organic molecules are described as contrast agents, including the range of Cyanines, Alexa, Atto, BODIPY, DyLight, Rhodamine, Fluorescein, Indocyanine green, etc. In addition, there are inorganic compounds such as QDOT that can be used for optical imaging in these optical ranges. The "visible" compounds in the optical ranges from 1000 to 1700 nm have the advantage of emitting in an optical range that improves resolution and detection depth compared to optical ranges below 1000 nm.

With the advent of these new cameras and various optical tools adapted to wavelengths between 1000 and 1700 nm (such as lenses), the development of adapted contrast agents becomes necessary.

There is therefore a real need to identify contrast agents that can be used with these new tools and thus greatly improve the quality of the images observed, more easily identify targeted cells (for example tumours), and broaden the range of detection in multi-fluorescence analyses.

It is to the applicant's credit that she has identified a class of fluorophore compounds, named aza-BODIPY, capable of emitting in the detection range 1000 to 1700 nm, alone, encapsulated or grafted to a molecule of interest (for example antibody or biological ligand), or a cell of interest (for example macrophage or stem cell).

The use of the contrast agents according to the invention also allows to follow the distribution of biological targets in tube, in vitro, in vivo or ex vivo.

Other advantages may become apparent to the person skilled in the art on reading the examples below, illustrated by the attached figures, which are given by way of illustration and are not limitative.

STATEMENT OF THE INVENTION

The invention relates to the use as a contrast agent in the optical window ranging from 1000 to 1700 nm of a fluorophore compound of formula I:

Formula I

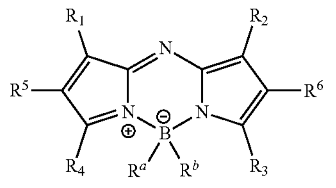

in which, $R^1$, $R^2$, $R^3$ and $R^4$, identical or different, represent a C5-C7 aryl or heteroaryl group, optionally substituted with at least one group chosen from halogen, —$NR^cR^d$, —$OR^d$, hydrazine, —$CF_3$ and —CN, at least one of $R^1$, $R^2$, $R^3$ and $R^4$ is a C5-C7 aryl group substituted with a —$NR^cR^d$ group, and optionally a group chosen from halogen, —$OR^d$, hydrazine, —$CF_3$ and —CN, $R^5$ and $R^6$, identical or different, represent a hydrogen, a halogen, a C1-C15 group comprising an aldehyde, ketone, carboxylic acid or ester function, a nitrile, —$SO_3Na$, a vinyl group optionally substituted by a ketone, ester or aromatic group, an imine substituted by an alkyl or aromatic group, an alkyne group optionally substituted by an alkyl or aromatic group, SPh, an aromatic chalcogen (SePh, TePh), an amide, a C5-C7 aryl or heteroaryl group, optionally substituted by at least one group chosen from a halogen, —$NR^cR^d$, —$OR^d$, hydrazine, —$CF_3$ and —CN, optionally $R^3$ and $R^5$ and/or $R^4$ and $R^6$ are covalently bonded and together form a C5-C7 aryl or heteroaryl group, optionally substituted with at least one group chosen from halogen, —$NR^cR^d$, —$OR^d$, hydrazine, —$CF_3$ and —CN, $R^c$ and $R^d$, identical or different, represent a hydrogen or a linear or branched C1-C3 alkyl chain, $R^a$ and $R^b$, identical or different, represent:

- a halogen, preferably chosen from the group comprising fluorine and chlorine,
- a C1-C50, aliphatic or heteroaliphatic, linear or branched, saturated or unsaturated group, optionally comprising one or more aromatic or heteroaromatic groups, optionally comprising one or more heteroatoms chosen from O, N, P and/or S, preferably in the form of one or more hydrophilic functions chosen from quaternary ammonium, sulphate, sulphonate and phosphonate functions a C1-C50, aliphatic or heteroaliphatic, linear or branched, saturated or unsaturated group, optionally comprising one or more aromatic or heteroaromatic groups, optionally comprising one or more heteroatoms chosen from O, N, P and/or S, preferably in the form of one or more bioconjugable functions chosen from amine, carboxylic acid, activated ester of the N-hydrosuccinimide type, pentafluorophenyl, tetrafluorophenyl, squarate and more particularly diethylsquarate, maleimide, thiol, isothiocyanate, isocyanate, oxadiazolyl methyl sulphone, azide, substituted or unsubstituted tetrazine, triazole, trans-cyclooctene, cyclooctyne and more particularly dibenzocyclooctyne, bicyclononyne and a $PPh_2AuCl$ complex, a biological vector covalently coupled via a C1-C50, aliphatic or heteroaliphatic, linear or branched, saturated or unsaturated group, optionally comprising one or more heteroatoms chosen from O, N, P and/or S, preferably in the form of one or more bioconjugable functions as defined above, a metal complex for therapeutic purposes, formed by a chelating agent and a metal, a radiometallic complex, formed by a chelating agent and a radiometal, or a molecule with a hydrodynamic diameter of less than 10 nm, a cyclic or linear peptide, an antibody, an antibody fragment, a nanobody, an affibody, an aptamer, a short DNA or RNA sequence, a sugar, a polysaccharide, an amino acid, a vitamin, an AMD3100 molecule, a PSMA ligand, a steroid (for example progesterone), a fatty acid (for example C4-C36), a polyamine (for example C4-C14), a polyphenol, a DNA base or a caffeine derivative.

Advantageously, the fluorophore compound may be in the form of a salt or a pharmaceutically acceptable salt.

In the context of the present invention, "optical window" means a wavelength range. The fluorophores used as contrast agents according to the invention can emit in an optical window ranging from 1000 to 1700 nm, preferably from 1000 to 1300 nm, and even more preferably from 1000 to 1100 nm.

"Biological target" means a cell, healthy or pathological, an organelle, a constituent of an animal or plant cell such as a protein, lipid, DNA/RNA, but also an antibody, a constituent of the extracellular matrix or a constituent of a biological fluid.

"Contrast agent" means a molecule or substance that artificially increases the contrast allowing the visualization of an anatomical (for example, an organ) or pathological (for example, a tumor) structure that is naturally low or non-contrast, and which would therefore be difficult to distinguish in its environment. In the context of the present invention, the contrast agents emit in the range from 1000 nm to 1700 nm, belonging to the very far infrared, also called NIR II or SWIR.

"BODIPYs" are compounds comprising the boron-dipyromethene unit, mainly known as strong UV-absorbing dyes with the property of emitting narrow fluorescence with high quantum yield. They are all derived from 4,4-difluoro-4-bora-3a, 4a-diaza-s-indacene:

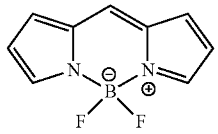 [SMILES: F[B-]1(F)n2cccc2C=C2C=CC=[N+]21]

"Aza-BODIPY" means BODIPY compounds comprising a nitrogen atom in position 8:

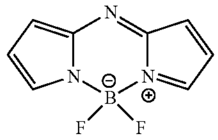 [SMILES: F[B-]1(F)n2cccc2N=C2C=CC=[N+]21]

For the purposes of this invention, "aliphatic" means non-aromatic groups. Aliphatic groups may be cyclic. Aliphatic groups may be saturated, such as hexane, or unsaturated, such as hexene and hexyne. Open chain groups (whether straight or branched) do not contain any type of cycle and are therefore aliphatic. Aliphatic groups can be saturated, connected by single bonds (alkanes) or unsaturated, with double bonds (alkenes) or triple bonds (alkynes). "Heteroaliphatic" groups are aliphatic groups with one or more heteroatoms, the most common being oxygen, nitrogen, phosphorus and sulphur.

The term "derivative" refers to a chemical compound or molecule made from a parent compound by one or more chemical reactions.

In general, the term "substituted" or "unsubstituted", whether or not preceded by the term "eventually" or "optionally", and the substituents contained in the formula of this invention refer to the replacement of the hydrogen radicals in a given structure with the radical of a specified substituent. Where more than one position in a given structure may be replaced by more than one substituent chosen from a given group, the substituent may be the same or different at each position. As used here, the term "substituted" is intended to include all permitted substituents of organic compounds.

As used here, the term "alkyl" refers to linear and branched alkyl groups. A similar convention applies to other generic terms such as "alkenyl", "alkynyl", etc. Illustrative alkyl groups include, but are not limited to, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, and the like, which may also bear one or more substituents. Alkenyl groups include, but are not limited to, ethenyl, propenyl, butenyl, 1-methyl-2-butenyl-2-1-yl, etc. Representative alkynyl groups include, but are not limited to, ethynyl, 2-propynyl (propargyl), 1-propynyl and others.

As used herein, the term "optionally including one or more heteroatoms" refers to groups bearing or having included in the main chain heteroatoms chosen from O, N, P and S.

In general, the term "unsaturated", as used here, refers to groups whose molecular structure contains one or more carbon-carbon double bonds or triple bonds.

In general, the terms "aromatic group", "aromatic cycle or heterocycle" or "aryl" or "heteroaryl", as used herein, refer to mono- or polycyclic unsaturated, stable, substituted or unsubstituted hydrocarbon groups, preferably having 3-14 carbon atoms, comprising at least one cycle satisfying the Hückel rule for aromaticity. Examples of aromatic groups are, but are not limited to, phenyl, indanyl, indenyl, indenyl, naphthyl, phenanthryl and anthracyl.

In general, “cyclic” as used herein refers to a 3-8-membered cyclic fragment, in the main chain or on a side chain, substituted or unsubstituted and optionally including one or more heteroatoms. Examples of such a heteroaryl group include, but are not limited to, the following: pyridinyl, thiazolyl, thiazolyl, thienyl, furanyl, pyrrolyl, pyrazolyl, imidazolyl, triazolyl, tetrazolyl, benzofuranyl, benzazepinyl, thianaphthalenyl, indolyl, indolinyl, quinolinyl, isoquinolinyl, benzimidazolyl, tetrahydroquinolinyl tetrahydroquinolinyl, tetrahydroisoquinolinyl, triazinyl, thianthrene, isobenzofuranyl, chromenyl, xanthenyl, phenoxanthinyl, isothiazolyl, isoxazolyl, pyrazinyl, pyridazinyl, indolizinyl, isoindolyl, indazolyl, purinyl, quinolinyl, phthalazinyl naphthyridinyl, quinoxalinyl, quinazolinyl, cinnolinyl, pteridinyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl imidazolinyl, pyrazolidinyl, pyrazolinyl, pyrazolinyl, indolinyl, isoindolinyl, oxazolidinyl, benzotriazolyl, benzisoxazolyl, oxindolyl, benzoxazolinyl, benzothienyl, benzothiazolyl, isatinyl, dihydropyridyl, pyrimidinyl, s-triazolinyl, oxazolyl and thiofuranyl.

Generally, the term “independently” refers to the fact that the substituents, atoms or groups to which these terms refer are chosen from the list of variables independently of each other (that means that they may be the identical or different).

The term “halogen” used herein refers to an atom chosen from fluorine, chlorine, bromine and iodine, preferably fluorine and chlorine.

A “bioconjugable function” is defined as a chemical function that allows the compounds of the invention to be covalently linked to a molecule of interest, and more particularly a molecule of biological interest, preferably a biological vector. Examples of such a function, without being limited to it, are the following: amine, carboxylic acid, activated ester of the N-hydrosuccinimide type, pentafluorophenyl, tetrafluorophenyl, squarate function and more particularly diethylsquarate, maleimide, thiol, isothiocyanate, isocyanate, oxadiazolyl methyl sulphone, azide, substituted or unsubstituted tetrazine, triazole, trans-cyclooctene, cyclooctyne type function and more particularly dibenzocyclooctyne, bicyclononyne and a $PPh_2AuCl$ complex.

“Biological vector” means any encapsulation system, or any ligand allowing the recognition of a specific biological target coupled covalently or not via a bioconjugable function.

By “chelating agent” is meant any chemical substance which has the property of permanently fixing ions to form a complex, and more particularly metal cations. This may include chelating agents of the polyamine family, whether cyclic or not.

“Radiometal” means a radioactive metal emitting for example gamma or beta+ radiation, such as Gallium-68 or Fluor-18 for example, or beta− or alpha radiation, such as Lutetium-177 or Actinium-225.

“Metal complex for therapeutic purposes” means any complex that includes an atom with therapeutic properties, on its own or after activation by an external or internal stimulus. It may be, for example, a complex chosen from $PR_2M$ (M=Ru(II), Os(II), Ru(III), Au(I) or (III), Pt(II), Pt(IV), Pd(II), Ir(III), Cu(I), Cu(II)) (R=alkyl, aryl, heteroaryl preferably triazaphosphaadamantane), carbene-M (M=Ru(II), Os(II), Ru(III), Au(I) or (III), Pt(II), Pt(IV), Ir(III), Cu(I), Cu(II)), phenylpyridine-M (M=Au(III), Pt(II), Ru(II), Ir(III), Re(V), Au(II), Pt(IV), Pd(II), Ir(III), Cu(II) Ir(III), Re(V), Re(III), Cu(II)), polypyridine (M=Au(III), Pt(II), Ru(II), Ir(III), Re(V), Re(III), Cu(II), Os(II)S-M (M=Au(I), Au(III), Cu(I), Cu(II), Ti(IV), Zr(IV), alkyne Au(I), dithiocarbamate-M (M=Au(I), Au(III), Cu(I), Cu(II), quinoline-M (M=Ga, Fe), η3-arene-M (M=Ru(II), Os(II), Cr (VI), Mo(III)), metallocene-M (M=Fe(II), Fe(III), Ti(IV), Ti(III), Zr(IV), Ir(III), Rh(III), Cr (VI), Ta(III), Os(II)), salen and salan-M (M=Au(III), Ti(IV), Zr(IV), Cu(II), Pt(II), Pd(II), malonate derivatives-M (M=Pt(II), Ti(IV)), ethylene diamine-M (M=Pt(II), Pd(II), Cu(II), Au(III), Ru(II), Os(II)), benzaldimine-M (M=Ru(II), Rh(III), Ir(III)).

Similarly, “radiometallic complex” means any complex containing a radioactive metal atom. The complex may be composed of a chelating agent chosen from the derivatives of DTPA, NOTA, NODAGA, DOTA, DOTAGA, p-NCS-Bn-DOTA, p-NCS-Bn-NOTA, DFO, sarcophagine, bridged cyclam, salan, salen, HBED, polypyridines of the bypyridine type, terpyridine, phenanthroline, phosphine or diphosphine polypyridines, carbene, arene, cyclopentadiene, alkyne, thiolate, phenylpyridine, phenyltriazole and a radiometal chosen from Ga68, Ga67, AlF18, In111, Zr89, Sc43, Sc44, Sm153, Cu61, Cu64, Co55, Co57, Tb152, Tb157, Ru103, Ru97, Ru95, Os191 Au198, Au199, Ti45, Pt195, Pt193, Pd100, Re186, Re188. It can be, for example, of the DOTA or NODAGA type and a radiometal chosen from Ga68 and In111 to obtain bimodal probes detectable in PET/SPECT and optical imaging or else chosen from Lu177, Y90, Ac225, Pb212, Bi212, Eb109, Yt161, Sc47, Cu67, Tb161, Os191, Pt195, Pt193, Au199, Pd103, Re186, Re188, Sm153 for theranostic applications; such as DOTAGA-111 In for example.

As understood by the person skilled in the art, all numbers, including those expressing quantities of ingredients, properties such as molecular weight, reaction conditions, etc., are approximations and are understood to be possibly modified in all cases by the term “about”. These values may vary according to the properties sought by those skilled in the art who use the teachings of the following descriptions. It is also understood that these values contain an inherent variability necessarily resulting from the standard deviations found in their respective test measurements.

The person skilled in the art will also readily recognize that when the members are grouped together in the same way, for example in a Markush group, the invention encompasses not only the whole of the listed group, but each member of the group individually and all possible subgroups of the main group. Furthermore, for all practical purposes, the invention encompasses not only the main group, but also the main group in the absence of one or more of the group members. The invention thus provides for the explicit exclusion of one or more members of a recited group.

Accordingly, reserves may apply to any of the disclosed categories or embodiments, whereby one or more of the recited elements, species or embodiments may be excluded from those categories or embodiments, for example, when used in an explicit negative limitation.

As used herein, the term “isomer” refers to compounds that may exist in one or more geometric, optical, enantiomeric, diastereomeric, epimeric, atropic, stereoisomeric, tautomeric, conformational or specific anomeric forms. Examples of isomers limited to cis- and trans-forms; E- and Z-forms; c-, t- and r-forms; c-, t- and r-forms; endo- and exo-forms; R-, S- and meso-forms; D- and L-forms; d- and I-forms; (+) and (−); keto-, enol- and enolate-forms; syn- and antiforms; synclinal and anticlinal forms; α- and β-forms; axial and equatorial forms; boat-, chair-, twist-, shell- and half-chair-forms; and combinations thereof, hereinafter collectively referred to as "isomers" (or "isomeric forms"). In the present disclosure, the term "isomer" excludes structural isomers or constitutional isomers that differ in constitution and are described by a different linear formula [2].

Advantageously, the fluorophore compound may be chosen from compounds of formula I wherein $R^1$, $R^2$, $R^3$ and $R^4$ are identical or different. $R^1$, $R^2$, $R^3$ and $R^4$ may independently represent a C5-C7 aryl or heteroaryl group. $R^1$, $R^2$, $R^3$ and $R^4$ may independently be optionally substituted with at least one group chosen from halogen, —$NR^cR^d$, —$OR^d$, hydrazine, —$CF_3$ and —CN.

The fluorophore compound may be chosen from compounds of formula I wherein at least one of $R^1$, $R^2$, $R^3$ and $R^4$ is a C5-C7 aryl group substituted with a —$NR^cR^d$ group and optionally a group chosen from a halogen, —$OR^d$, hydrazine, —$CF_3$ and —CN. Preferably, when it is a C6 aryl group, the —$NR^cR^d$ group is in the para position.

Advantageously, the fluorophore compound is chosen from compounds of formula I wherein $R^5$ and $R^6$ are identical or different. $R^5$ and $R^6$ can independently represent a hydrogen, a halogen, a C1-C15 group comprising an aldehyde, ketone, carboxylic acid or ester function, a nitrile, —$SO_3Na$, a vinyl group optionally substituted by a ketone, ester or aromatic group, an imine substituted by an alkyl or aromatic group, an alkyne group optionally substituted by an alkyl or aromatic group, SPh, an aromatic chalcogen (SePh, TePh), an amide, a C5-C7 aryl or heteroaryl group, optionally substituted by at least one group chosen from halogen, —$NR^cR^d$, —$OR^d$, hydrazine, —$CF_3$ and —CN. Preferably, $R^5$ and $R^6$ are hydrogen or —$SO_3Na$.

Advantageously, the fluorophore compound is chosen from compounds of formula I wherein $R^c$ and $R^d$ are identical or different. $R^c$ and $R^d$ may independently represent a hydrogen or a linear or branched C1-C3 alkyl chain. Preferably, —$NR^cR^d$ is chosen from the group comprising —NH2, —$NMe_2$, —$NEt_2$, —$NPr_2$, preferably —$NMe_2$.

Advantageously, $R^3$ and $R^5$ and/or $R^4$ and $R^6$ may be covalently bonded and together form a C5-C7 aryl or heteroaryl group, optionally substituted with at least one group chosen from halogen, —$NR^cR^d$, —$OR^d$, hydrazine, —$CF_3$ and —CN.

Advantageously, the fluorophore compound may be chosen from compounds of formula I wherein $R^5$ and $R^6$ are a hydrogen.

Advantageously, the fluorophore compound may be chosen from compounds of formula I in which $R^1$ and $R^2$, identical or different, represent a C5-C7 aryl group substituted by a —$NR^cR^d$ group and optionally a group chosen from a halogen, —$OR^d$, hydrazine, —$CF_3$ and —CN. Preferably, the fluorophore compound can be chosen from compounds of formula I wherein $R^1$ and/or $R^2$ represent a phenyl group substituted by a —$NR^cR^d$ group, preferably in the para position.

Advantageously, the fluorophore compound may be chosen from compounds of formula I wherein $R^a$ and $R^b$ are identical or different. $R^a$ and $R^b$ may represent halogen, preferably fluorine or chlorine.

Advantageously, the fluorophore compound may be chosen from compounds of formula I wherein $R^a$ and $R^b$ are identical or different. $R^a$ and $R^b$ may represent a C1-C50, preferably C2-C30 aliphatic or heteroaliphatic, linear or branched, saturated or unsaturated group, optionally comprising one or more aromatic or heteroaromatic groups, optionally comprising one or more heteroatoms chosen from O, N, P and/or S, preferably in the form of one or more hydrophilic functions chosen from quaternary ammonium, sulphate, sulphonate and phosphonate functions.

Advantageously, the fluorophore compound may be chosen from compounds of formula I wherein $R^a$ and $R^b$ are identical or different. $R^a$ and $R^b$ may represent a C1-C50, preferably C5-C30, aliphatic or heteroaliphatic, linear or branched, saturated or unsaturated group, optionally comprising one or more aromatic or heteroaromatic groups, optionally comprising one or more heteroatoms chosen from O, N, P and/or S, preferably in the form of one or more bioconjugable functions chosen from amine, carboxylic acid, activated ester of the N-hydrosuccinimide type, pentafluorophenyl, tetrafluorophenyl, squarate and more particularly diethylsquarate, maleimide, thiol, isothiocyanate, isocyanate, oxadiazolyl methyl sulphone, azide, substituted or unsubstituted tetrazine, triazole, trans-cyclooctene, cyclooctyne and more particularly dibenzocyclooctyne and bicyclononyne and a $PPh_2AuCl$ complex.

Advantageously, the fluorophore compound may be chosen from compounds of formula I wherein $R^a$ and $R^b$ are identical or different. $R^a$ and $R^b$ may represent a biological vector covalently coupled via a group comprising a bioconjugable function as defined above.

Advantageously, the fluorophore compound is chosen from the compounds of formula I in which $R^a$ and or $R^b$, identical or different, comprise a $^{10}$BSH ($Na_2B_{12}H_{11}SH$ or sodium borocaptate, enriched in boron10), for obtaining theranostics active in borotherapy (boron neutron capture therapy, or BNCT).

Advantageously, the fluorophore compound may be chosen from compounds of formula I wherein $R^a$ and $R^b$ are identical or different. $R^a$ and $R^b$ may represent a metal complex for therapeutic purposes, preferably chosen from complexes of formula $PR_2M$ wherein M is a metal chosen from the group comprising Ru(II), Os(II), Ru(III), Au(I) or (III), Pt(II), Pt(IV), Pd(II), Ir(III), Cu(I), Cu(II) and R is C1-12 alkyl, aryl, heteroaryl, preferably triazaphosphaadamantane, carbene-M wherein M is a metal chosen from the group comprising M=Ru(II), Os(II), Ru(III), Au(I) or (III), Pt(II), Pt(IV), Ir(III), Cu(I), Cu(II), phenylpyridine-M wherein M is a metal chosen from the group comprising Au(III), Pt(II), Ru(II), Ir(III), Re(V), Re(III), Cu(II), polypyridine-M wherein M is a metal chosen from the group consisting of Au(III), Pt(II), Ru(II), Ir(III), Re(V), Re(III), Cu(II), Os(II), S-M wherein M is a metal chosen from the group consisting of Au(I), Au(III), Cu(I), Cu(II), Ti(IV), Zr(IV) alkyne-Au(I), dithiocarbamate-M wherein M is a metal chosen from the group comprising Au(I), Au(III), Cu(I), Cu(II), quinoline-M wherein M is a metal chosen from the group comprising Ga, Fe, η3-arene-M wherein M is a metal chosen from the group comprising Ru(II), Os(II), Cr (VI), Mo(III)), metallocene-M wherein M is a metal chosen from the group comprising Fe(II), Fe(III), Ti(IV), Ti(III), Zr(IV), Ir(III), Rh(III), Cr (VI), Ta(III), Os(II), salen and salan-M wherein M is a metal chosen from the group consisting of Au(III), Ti(IV), Zr(IV), Cu(II), Pt(II), Pd(II), malonate derivatives-M wherein M is a metal chosen from the group consisting of Pt(II), Ti(IV) ethylene diamine-M wherein M is a metal chosen from the group consisting of Pt(II), Pd(II), Cu(II), Au(III), Ru(II), Os(II), benzaldimine-M wherein M is a metal chosen from the group consisting of Ru(II), Rh(III), Ir(III).

Advantageously, the fluorophore compound may be chosen from compounds of formula I wherein $R^a$ and $R^b$ are identical or different. $R^a$ and $R^b$ may represent a radiometallic complex formed by a chelating agent and a radiometal.

The complex may be composed of a chelating agent chosen from the derivatives of DTPA, NOTA, NODAGA, DOTA, DOTAGA, p-NCS-Bn-DOTA, p-NCS-Bn-NOTA, DFO, sarcophagine, bridged cyclam, salan, salen, HBED, bipyridine, terpyridine, phenanthroline, phosphine or diphosphine, carbene, arene, cyclopentadiene, alkyne, thiolate, phenylpyridine, phenyltriazole and a radiometal chosen from Ga68, Ga67, AIF18, In111, Zr89, Sc43, Sc44, Sm153, Cu61, Cu64, Co55, Co57, Tb152, Tb157, Ru103, Ru97, Ru95, Os191 Au198, Au199, Ti45, Pt195, Pt193, Pd100, Re186, Re188. It can be, for example, of the DOTA or NODAGA type and a radiometal chosen from Ga68 and In111 to obtain bimodal probes detectable in PET/SPECT and optical imaging or else chosen from Lu177, Y90, Ac225, Pb212, Bi212, Eb109, Yt161, Sc47, Cu67, Tb161, Os191, Pt195, Pt193, Au199, Pd103, Re186, Re188, Sm153, for theranostic applications Advantageously, the fluorophore compound can be chosen from compounds of formula I in which $R^a$ and $R^b$, identical or different, are chosen from a small molecule, that means a molecule with a hydrodynamic diameter of less than 10 nm such as gold clusters or metal complexes, a cyclic or linear peptide (such as $\alpha_v\beta_3$ integrin-targeting c(RGDfK) or neuropilin-targeting ATWLPPR), an antibody (for example anti-CD44 type), an antibody fragment or a nanobody targeting a membrane or intracellular receptor, an affibody, an aptamer, a short DNA or RNA sequence, a sugar (as for example a thioglucose or peracetylated thioglucose) or a polysaccharide, an amino acid, a vitamin (for example folic acid type), a ligand of the type AMD3100, a PSMA ligand, a steroid, a fatty acid, a polyamine (for example spermine, spermidine, cadaverine or putrescine type), a polyphenol (for example resveratrol), a DNA base, a caffeine derivative, progesterone.

Advantageously, the fluorophore compound can be chosen from compounds of formula I in which $R^a$ and $R^b$, identical or different, are chosen from halogen, preferably fluorine.

Advantageously, the fluorophore compound can be chosen from compounds of formula I in which $R^a$ and $R^b$, identical or different, are chosen from hydrophilic groups of the following formulae:

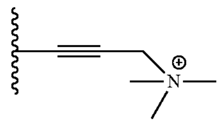

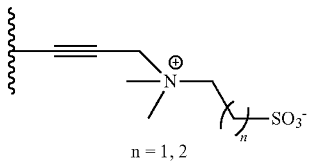

n = 1, 2

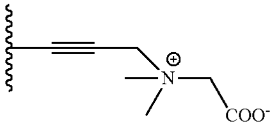

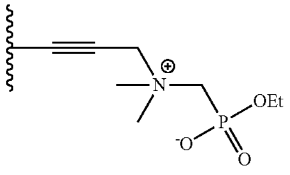

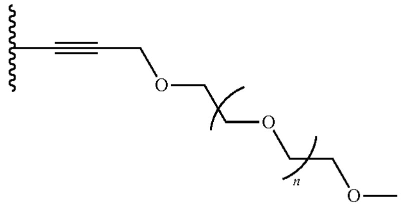

n = 1 to 10

-continued

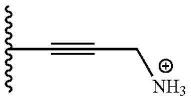

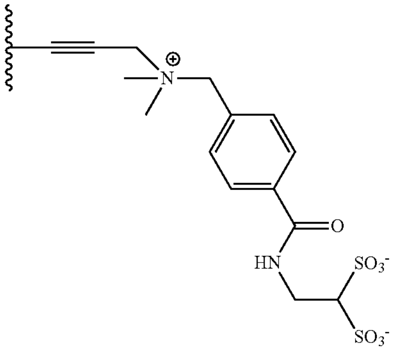

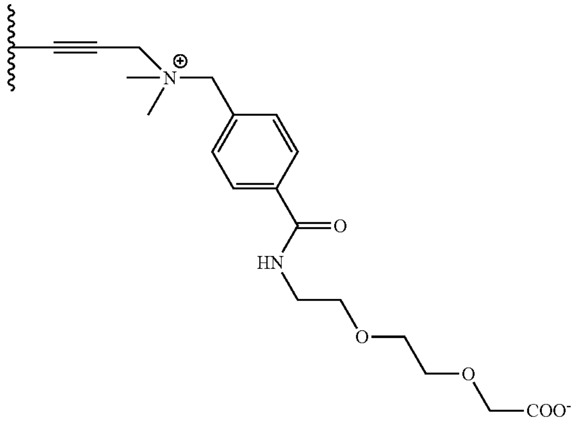

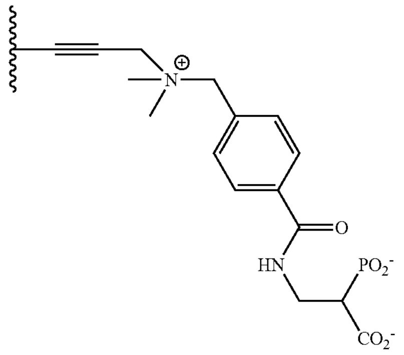

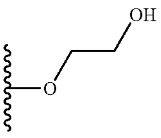

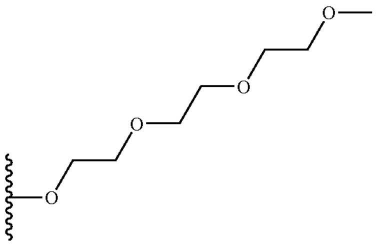

-continued

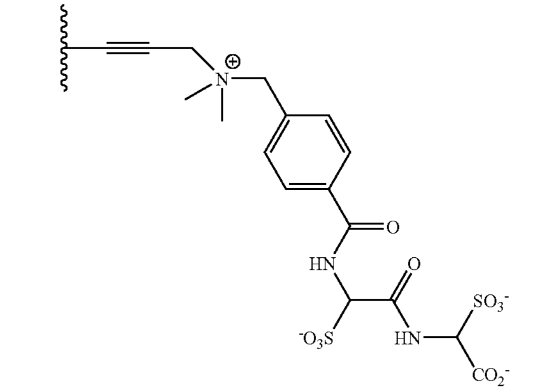

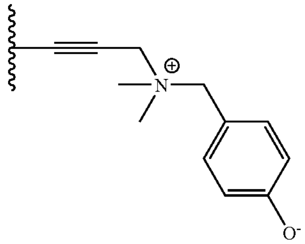

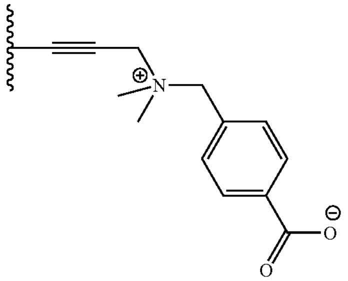

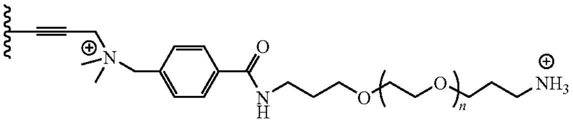

$n$ = 1 to 12

In the present application, the symbol , represents the point of attachment of the represented group to the molecule. For example, it may be the point of attachment to B (boron atom).

Advantageously, the fluorophore compound can be chosen from compounds of formula I in which $R^a$ and $R^b$, identical or different, are chosen from groups comprising a bioconjugable function of the following formulae:

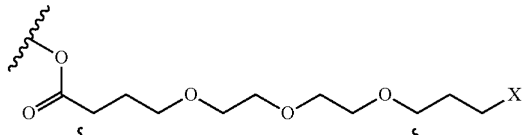

or

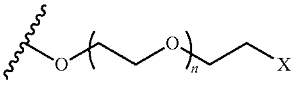

n = 1 to 12 or

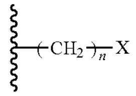

n = 1 to 12

X = $NH_2$ $N_3$

-continued

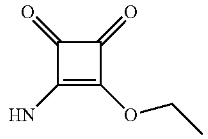

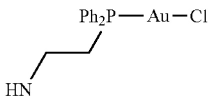

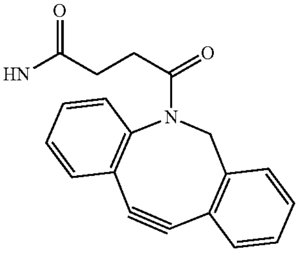

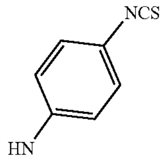

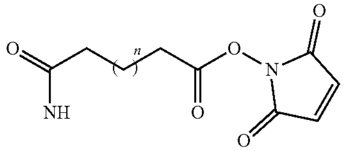

n = 1, 4

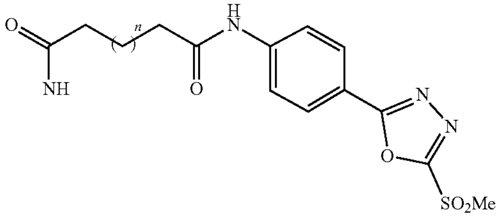

n = 1, 4

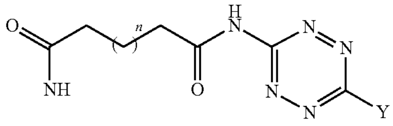

n = 1, 4

Y = H, Cl, Me

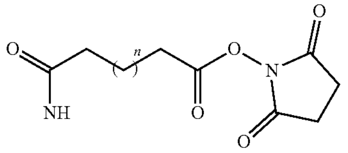

n = 1, 4

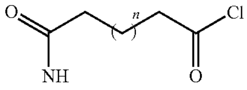

n = 1, 4

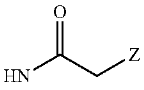

Z = Br, Cl, I

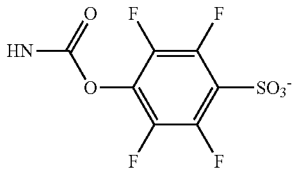

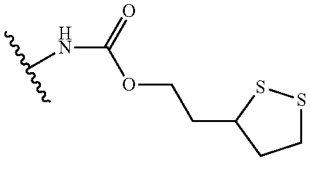

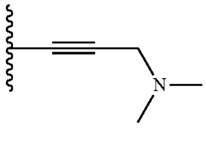

-continued

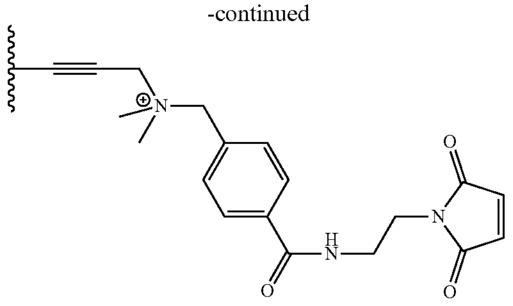

—$NH_2$ and —$Si(OMe)_3$.

Preferably, the bioconjugable function can be chosen from N-hydroxysuccinimide, conjugated isothiocyanate, tetrazine, diethylsquarate, maleimide, oxadiazolyl methyl sulfone, pentafluorophenyl, azide, a $PPh_2AuCl$ complex and $NH_2$ functions.

Advantageously, the fluorophore compound may be chosen from compounds of formula I, wherein $R^a$ and/or $R^b$ comprise a covalently coupled biological vector and respond, for example of the following formula:

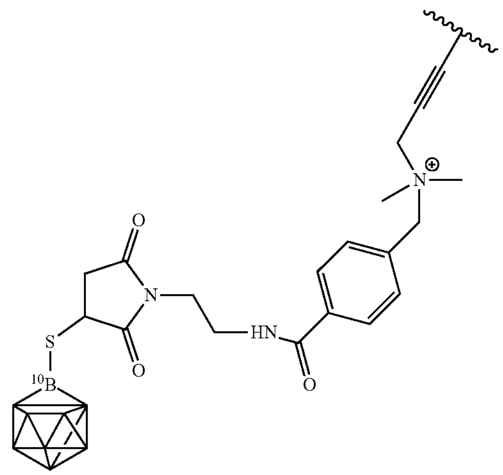

Advantageously, the fluorophore compound can be chosen from compounds of formula I in which $R^a$ and R b, identical or different, are chosen from $PPh_2$-Au(I), $PPh_2$-Pt (II), $PPh_2$-Pt(IV), phneylpyridine-Au(III). Advantageously, the fluorophore compound can be chosen from compounds of formula I in which $R^a$ and $R^b$, identical or different, are chosen from DOTA-In(III), DOTAGA-In(III), NODAGA-Cu(II), NODAGA-Ga(III).

Advantageously, the fluorophore compound can be chosen from compounds of formula I in which $R^a$ and $R^b$, identical or different, are chosen from a cyclic or linear peptide (such as $\alpha_v\beta 3$ integrin-targeting c(RGDfK) or neuropilin-targeting ATWLPPR), an antibody (for example anti-CD44 type), an antibody fragment or a nanobody targeting a membrane or intracellular receptor, a short DNA or RNA sequence, a sugar (as for example a thioglucose or peracetylated thioglucose) or a polysaccharide, an amino acid, a vitamin (for example folic acid type), an AMD3100 type-ligand, a PSMA type-ligand, a steroid (for example progesterone) a fatty acid (for example C4-C36), a polyamine (for example spermine, spermidine, cadaverine or putrescine type), a polyphenol (for example resveratrol), a DNA base, a caffeine derivative (for example caffeine).

Advantageously, the fluorophore compound can be chosen from compounds of formula I in which $R^a$ and $R^b$, which may be identical or different, are chosen from a cyclic or linear peptide ($\alpha_v\beta_3$ integrin-targeting c(RGDfK) or neuropilin-targeting ATWLPPR), an antibody (for example of the anti-CD44 type), an antibody fragment targeting a membrane or intracellular receptor, a short DNA or RNA sequence, a sugar (as for example a thioglucose or peracetylated thioglucose) or a polysaccharide, an amino acid, a vitamin (for example folic acid type), an AMD3100 ligand, a steroid (for example progesterone), a fatty acid (for example C4-C36), a polyamine (for example spermine, spermidine, cadaverine or putrescine type), a polyphenol (for example resveratrol), a DNA base, a caffeine derivative (for example caffeine).

Advantageously, the fluorophore compound can be chosen from compounds of formula I in which $R^a$ and $R^b$, identical or different, are chosen from the groups of the following formulae:

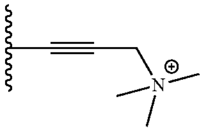

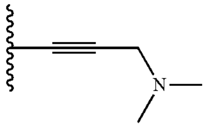

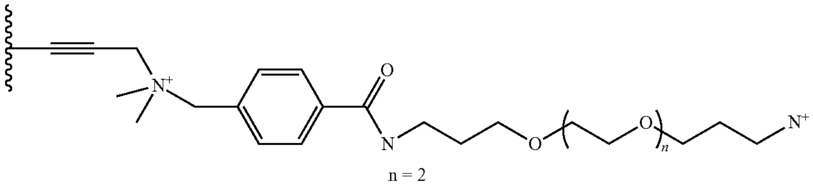

n = 2

-continued

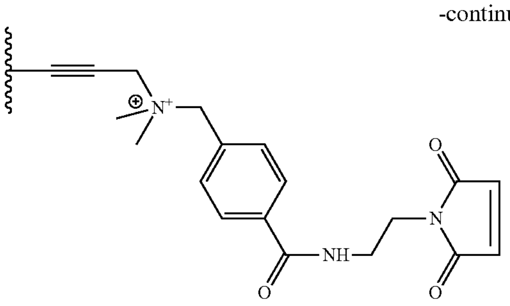

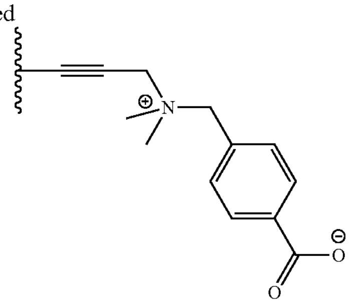

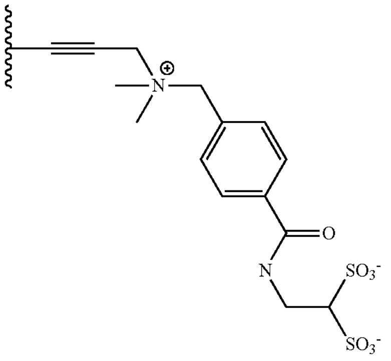

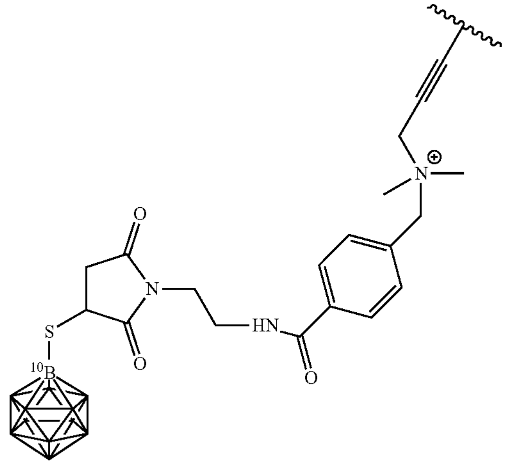

Advantageously, the fluorophore compound may be chosen from fluorophore compounds of formula I wherein $R^5$ and $R^6$ are H, $R^1$ and $R^2$ are

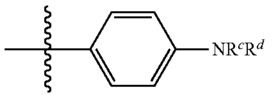

and $R^3$ and $R^4$ are respectively

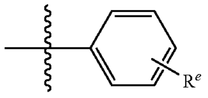

and

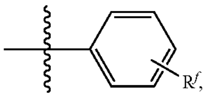

of formula II:

Formula II

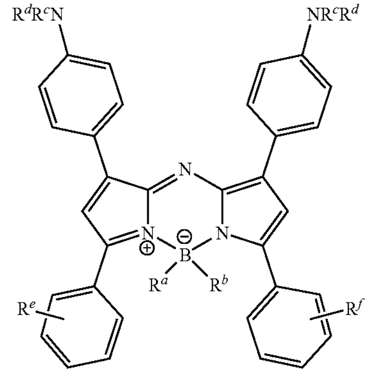

in which, $R^a$, $R^b$, $R^c$, $R^d$ have the definitions given above, $R^e$ and $R^f$, identical or different, represent at least one of hydrogen, halogen, —$NR^cR^d$, —$OR^d$, hydrazine, —$CF_3$ and —CN.

Advantageously, the fluorophore compound may be chosen from compounds of formula I or II wherein $R^c$ and $R^d$ are —$CH_3$.

Advantageously, the fluorophore compound can be chosen from compounds of formula II in which $R^e$ and $R^f$ are H or —OMe, preferably in the para position.

Advantageously, the fluorophore compound may be included in a composition further comprising a pharmaceutically acceptable excipient and/or a solvent. This may be any pharmaceutically acceptable excipient that the person skilled in the art may put in the composition to modify its pH, osmolarity, viscosity or solubility. Examples include NaCl (aqueous at 0.9%), 5 g/L glucose solutions, ppi water or buffered solutions such as PBS or other pharmaceutically acceptable buffers.

Advantageously, the composition may have a pH in the range from 4 to 10, preferably from 6 to 8 or from 6.8 to 7.6. Preferably the pH of the composition is 7.4.

Advantageously, the concentration of the fluorophore compound in the composition is in the range from 0.1 to 1000 μmol/L, preferably 1 to 100 μmol/L or 10 to 40 μmol/L (these values are in particular compatible with in vitro detections) or in the range from 4 nmol/kg to 300 μmol/kg in mice, preferably 40 nmol/kg to 12.5 μmol/kg, or around 1 to 1.5 μmol/kg (these values are in particular compatible with in vivo detections).

Advantageously, the fluorophore compound can be encapsulated. In the context of the invention, "encapsulated" means any biologically compatible object that makes it possible to group together and possibly protect several fluorophore compounds and to conduct them to the target of interest, such as lipid nanoparticles, nanoformulations in particular based on polysaccharides, carbon nanotubes, micelles. For example, the fluorophore compound can be encapsulated in a lipophilic formulation comprising a liposome as described in Gravier et al publication [3], a lipid capsule as described in Hirsjärvi et al publication [4] or hydrophobic nanodomains such as the polysaccharide nanoformulations described in Garcia et al publication [5].

Advantageously, the fluorophore compound may be covalently linked to a nanoparticle. The coupling can be carried out via the $R^a$ or $R^b$ group carrying a bioconjugable function as defined above. The nanoparticles that can be covalently linked to the compound of formula I or II may be of the type of small nanoparticles with sizes below 10 kDa, or lipid nanoparticles. These may be, for example, gold nanoclusters or lipidots.

The invention also relates to a kit comprising an injection system, and a composition comprising a fluorophore compound of formula I or II as defined above and a pharmaceutically acceptable excipient and/or solvent.

The invention also relates to a method for in vitro identification of a biological target (such as a healthy or tumour cell, protein, DNA, RNA for example) comprising at least the steps of:

- labelling the cells of a sample taken or cultured with a composition comprising a fluorophore compound of formula I or II as defined above,
- measurement of fluorescence in the optical window comprise in a range from 1000 to 1700 nm, and
- identification of target cells.

Advantageously, in the in vitro identification method according to the invention, the fluorophore concentration in the composition is in a range from 0.1 to 1000 μmol/L, preferably 1 to 100 μmol/L or 10 to 40 μmol/L.

Advantageously, the labelling of the cells of the sample is carried out by injection or by spraying of the composition comprising the fluorophore.

Advantageously, the measurement of the fluorescence in the optical window comprised in an interval from 1000 to 1700 nm is carried out by any means known to the person skilled in the art and capable of measuring said fluorescence. This may be, for example, confocal microscopy or epifluorescence flow cytometry, optical imaging by fluorescence reflection (2D or 3D) or even by an optical probe to assist surgery or adapted to the reading of multi-well plates.

The invention also relates to a method for in vivo identification of a biological target (such as a healthy or tumour cell, protein, DNA, RNA for example) comprising at least the steps of:

- labelling the cells of a subject by injection or spraying with a composition comprising a fluorophore compound of formula I or II as defined above,
- measurement of fluorescence in the optical window comprises in a range from 1000 to 1700 nm, and
- identification of target cells.

Advantageously, in the in vivo identification method according to the invention, the fluorophore concentration in the composition is in the range from 4 nmol/kg to 300 μmol/kg in mice, preferably 40 nmol/kg to 12.5 μmol/kg, or around 1 to 1.5 μmol/kg.

Advantageously, the labelling of the cells of the sample is carried out by injection or by spraying of the composition comprising the fluorophore.

Advantageously, the measurement of the fluorescence in the optical window comprised in an interval from 1000 to 1700 nm is carried out by any means known to the person skilled in the art and capable of measuring said fluorescence. This may be, for example, epifluorescence or confocal microscopy, flow cytometry, optical imaging by fluorescence reflection (2D or 3D) or even by a portable optical probe such as those used to assist surgery, or adapted to a plate reader.

The in vivo model used herein is based on mice. Advantageously, in the method according to the invention, the fluorophore concentration in the composition administered in vivo is in the range from 4 nmol/kg to 300 μmol/kg in mice, preferably 40 nmol/kg to 12.5 μmol/kg, or around 1 to 1.5 μmol/kg. Any other administration may be done according to interspecies conversions, as described for example in the article by Reagan-Shaw et al [6]

In a non-limiting way, we can mention the advantages linked to the invention:

- increase in the quality of the images observed, improvement in the resolution of the images (compared to NIR imaging),
- easier identification of tumor cells, including the observation of tumors in vivo,
- Deep tissue detection of the biological target,
- possibility of monitoring the distribution of biological targets in tubes, in vitro or in vivo,
- increase the wavelength range usable in multi-labelling analyses,
- extension of the range of fluorescent compounds in multiple markings,
- enable imaging in the optical range above 1000 nm called SWIR or very far infrared,
- also allow this imaging technique to be coupled with photoacoustic imaging,
- reduced scattering and autofluorescence of tissues.

Furthermore, according to the invention, the optical contrast agent can be used alone, or coupled to a molecule of interest, or encapsulated in a nano-formulation.

EXAMPLES

Figure 1:
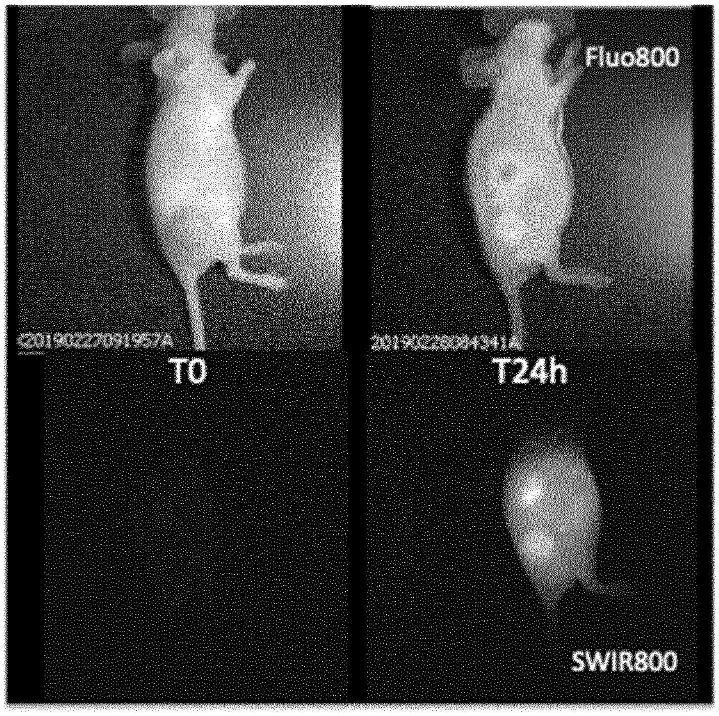
FIG. 1 shows a mouse with a U87MG tumour in the right hind leg before and 24 hours after injection of aza-BODIPY (AG22). The upper planes are recorded in NIR imaging: Fluo800 corresponds to excitation at 780 nm and collection between 830-900 nm. The lower planes are excited at 830 nm (SWIR800) and the emission is collected using a 1064 nm long pass filter, that means between 1064 and 1700 nm.
Figure 2:
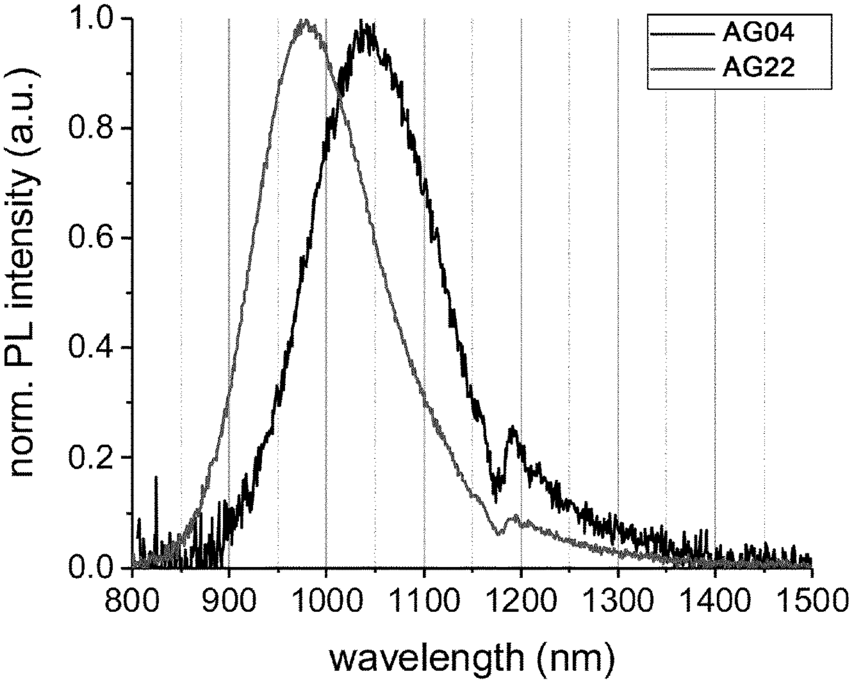
FIG. 2 shows the emission spectra of compounds AG22 and AG04.
Figure 3:
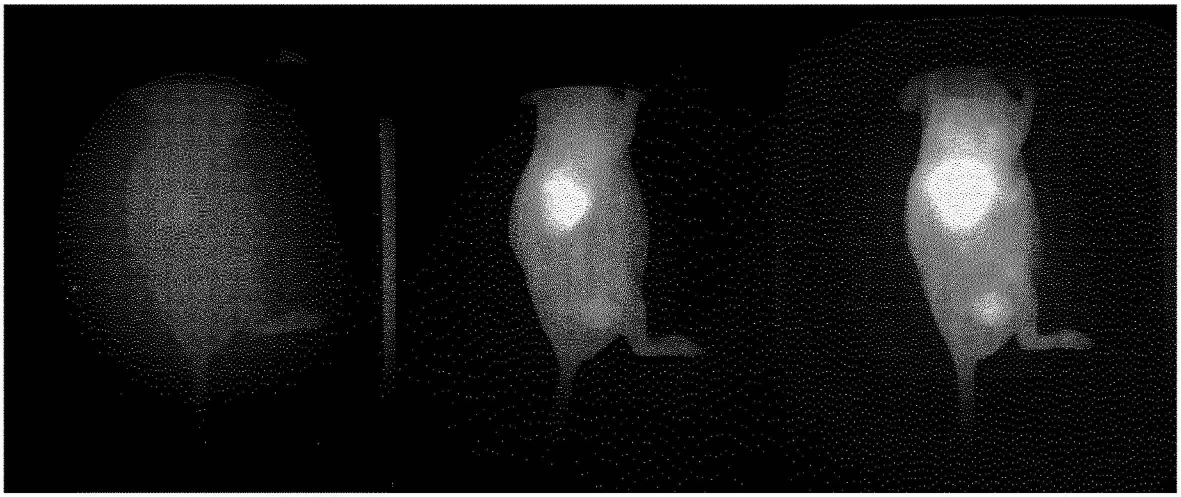
FIG. 3 shows a mouse with a U87MG tumour in the right hind leg, from left to right: before, at 5 h and at 48 h after injection of the AG66 compound.

Example 1: Synthesis of Contrast Agents According to the Invention

Materials & Methods

The reactions were carried out in technical grade Carlo Erba solvents under normal atmosphere, unless otherwise stated. Experiments requiring anhydrous conditions were carried out under argon. Dry solvents were purchased from Carlo Erba, unstabilised and were dried using MB-SPS-800 (MBraun) or PureSolv-MD-5 (Inert®). All commercial reagents were purchased from Sigma-Aldrich® or ACROS Organics® and were used as received without any purification. TOTA-Boc (boc-1-amino-4,7,10-trioxa-13-tridecanamine) was purchased from Iris Biotech GmbH® and $^{10}B$-BSH from Katchem®. Reaction monitoring was performed by HPLC-MS and thin layer chromatography on 0.2 mm thick Merck® 60 F254 silica gel plates, revealed by UV (254 nm). Chromatography column purifications were performed on Sigma-Aldrich® technical silica gel, 40-63 μm, 230-400 mesh, 60 Å.

NMR spectra ($^1H$, $^{13}C$) were recorded on a Bruker 500 Avance III or Bruker 600 Avance III HD (equipped with dual resonance broadband probes). Chemical shifts are expressed in ppm and are given relative to TMS ($^1H$, $^{13}C$) with the residual solvent signal as reference. High resolution mass spectra were recorded on a Thermo LTQ Orbitrap XL ESI-MS spectrometer. NMR and mass analysis were performed at the Plateforme d'Analyse Chimique et de Synthèse Moléculaire de l'Université de Bourgogne (PACSMUB).

HPLC-MS analyses were performed on a Thermo-Dionex Ultimate 3000 instrument (pump+autosampler at 20° C.+column oven at 25° C.) equipped with a diode array detector (Thermo-Dionex DAD 3000-RS) and a simple MSQ Plus quadrupole mass spectrometer equipped with a Phenomenex Kinetex® column (2.6 μm, C18, 100 Å, LC 50×2.1 mm column). The gradient used for the characterisation was as follows (Gradient A):

| Time (min) | % H2O (+ 0.1% formic acid) | % ACN (+ 0.1% formic acid) | Flow rate (mL/min) |
|---|---|---|---|
| 0 | 95 | 5 | 0.5 |
| 5 | 0 | 100 | 0.5 |
| 6.5 | 0 | 100 | 0.5 |
| 6.6 | 95 | 5 | 0.5 |
| 8.5 | 95 | 5 | 0.5 |
| 8.51 | 95 | 5 | 0.05 |

Semi-preparative HPLC purifications were performed on a Shimadzu HPLC instrument equipped with 2 LC-20AT pumps, a SPD-20A UV/Vis detector, a FRC-10A fraction collector, a SIL-10AP sampler and a CBM-20A control unit. The column used is a Shim-Pack GIST 5 μm C18 10×250 mm column and the gradients used are as follows:

| Gradient A | | | | Gradient B | | | |
|---|---|---|---|---|---|---|---|
| Time (min) | % H2O + 0.1% TFA | % ACN + 0.1% TFA | Flow rate (mL/min) | Time (min) | % H2O + 0.1% TFA | % ACN + 0.1% TFA | Flow rate (mL/min) |
| 0 | 75 | 25 | 5 | 0 | 60 | 40 | 5 |
| 5 | 75 | 25 | 5 | 5 | 80 | 40 | 5 |
| 25 | 0 | 100 | 5 | 25 | 0 | 100 | 5 |
| 28 | 0 | 100 | 5 | 28 | 0 | 100 | 5 |
| 30 | 75 | 100 | 5 | 30 | 80 | 40 | 5 |
| **Gradient C** | | | | **Gradient D** | | | |
| Time (min) | % H2O + 0.1% TFA | % ACN + 0.1% TFA | Flow rate (mL/min) | Time (min) | % H2O + 0.1% TFA | % ACN + 0.1% TFA | Flow rate (mL/min) |
| 0 | 80 | 20 | 5 | 0 | 80 | 20 | 5 |
| 5 | 80 | 20 | 5 | 5 | 80 | 20 | 5 |
| 28 | 0 | 100 | 5 | 25 | 0 | 100 | 5 |
| 33 | 0 | 100 | 5 | 27 | 0 | 100 | 5 |
| 35 | 80 | 20 | 5 | 28 | 80 | 20 | 5 |

Compound AG22

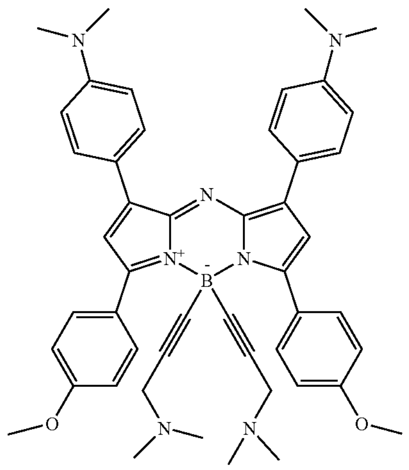

Compound AG24

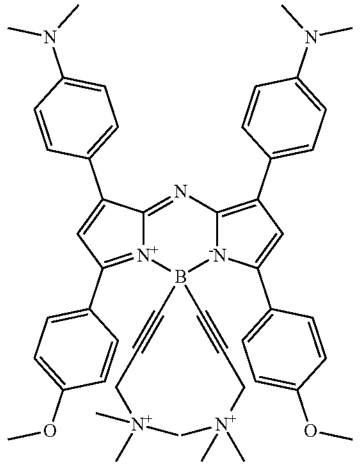

1.6 $CF_3COO^-$
0.4 $I^-$

18 μL of N,N-dimethylpropargylamine (156 μmol, 2 eq) is dissolved in 2 mL of THF (tetrahydrofuran) under argon (shlenk glassware). Magnesium ethyl bromide (0.17 mL, 170 μmol, 2.2 eq) is then added and the mixture is refluxed for 45 min, allowed to return to room temperature, then transferred via cannula to a second schlenk containing the aza-BODIPY precursor (50 10 mg, 78 μmol, 1 eq). The mixture is then stirred at reflux for 45 min under argon, then the reaction is stopped by adding 2 mL of EtOH. The solvents are removed by evaporation under reduced pressure. The crude formed is solubilized in 10 mL of AcOEt, then 10 mL of distilled water is added. After stirring and settling in a separating funnel, the organic phase is set aside and the aqueous phase is extracted twice with 10 mL AcOEt. The organic phases are combined, washed twice with 10 mL twice-diluted aqueous $NaHCO_3$ solution and dried over anhydrous $MgSO_4$. The resulting solution is filtered and the solvent is removed by evaporation under reduced pressure. The residue is purified by silica gel chromatography column (eluent: 98/2 DCM/MeOH→100% MeOH) to isolate AG22 as a purple glittery powder (51.1 mg, 66.3 μmole, 85%).

$^1$H NMR ($CDCl_3$, 500 MHz) δ (ppm): 8.18 (d; $^3J$=8.9 Hz; 4H); 8.05 (d; $^3J$=9.0 Hz; 4H); 6.97 (d; $^3J$=9.0 Hz; 4H); 6.77 (d; $^3J$=8.9 Hz; 4H); 6.77 (s; 2H); 3.86 (s; 6H); 3.27 (s; 4H); 3.08 (s; 12H); 2.26 (s; 12H).

$^{13}$C NMR {1H} ($CDCl_3$, 150 MHz) δ (ppm): 160.8; 156.5; 150.8; 143.0; 142.4; 132.0; 130.6; 125.6; 121.0; 115.6; 113.4; 112.0; 55.4; 48.0; 42.3; 40.2

HR-MS (ESI) (Da): m/z calculated for $C_{48}H_{52}BN_7O_2$ $[M+H]^+$ 770.42755; found 770.43559.

Analytical HPLC (Gradient A): Tr=4.46 min.

AG22 (30 mg, 39 μmol, 1 eq) is dissolved in 3 mL DCM (dichloromethane). Iodomethane (1.5 mL, large excess) is then added and the reaction medium is stirred for 1 h at room temperature. The solvents are then removed under reduced pressure and the crude obtained is solubilised in 10 ml of a $H_2O$/DCM mixture (1/1). An extraction of the aqueous phase with DCM (3×5 mL) is carried out, then in a second step the organic phase obtained is extracted with water (8×10 mL). The recovered aqueous phase is evaporated, and the precipitate formed is purified by HPLC (Gradient A). The solid obtained is freeze-dried to provide pure AG24 as a blue-green solid (17.8 mg, 17.2 μmol, 44%).

$^1$H NMR (DMSO, 500 MHz) δ (ppm): 8.24 (d; $^3J_{He-Hf}$=8.9 Hz; 4H); 8.10 (d; $3J_{Hb-Hc}$=9.0 Hz; 4H); 7.22 (s; 2H); 7.11 (d; $^3J_{Hb-Hc}$=9.0 Hz; 4H); 6.86 (d; $^3J_{He-Hf}$=8.9 Hz; 4H); 4.00 (s; 4H); 3.87 (s; 6H); 3.07 (s; 12H); 2.78 (s; 18H).

HR-MS (ESI) (Da): m/z=calculated for $C_{50}H_{58}BN_7O_2^{2+}$ $[M]^{2+}$ 399.73670; found 399.73869.

Analytical HPLC (Gradient A): Tr=4.49 min.

Compound AG38

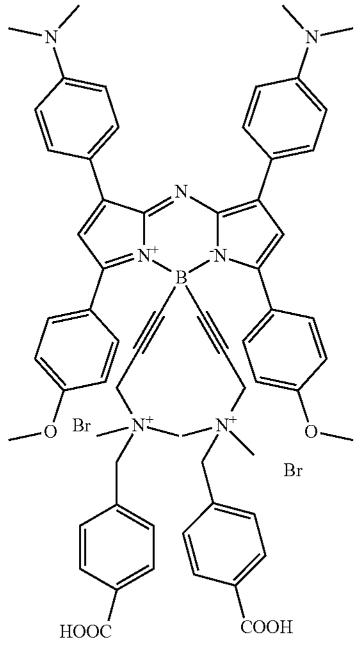

Compound AG57

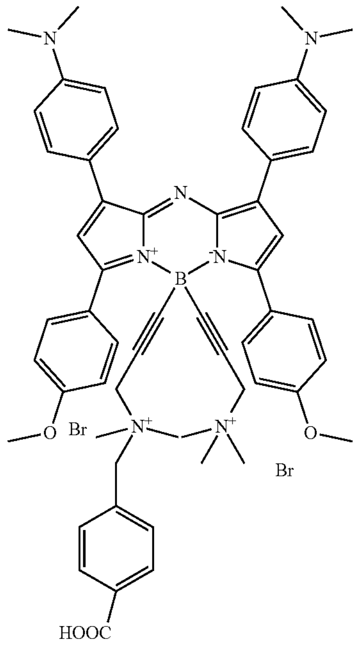

AG22 (250 mg, 0.32 mmol, 1 eq) is dissolved in 50 mL THF and 8 mL $H_2O$. $NaHCO_3$ (137 mg, 1.63 mmol, 5.1 eq) is added followed by 4-bromoethylbenzoic acid (144 mg, 0.67 mmol, 2.1 eq). The reaction mixture is left to stir at room temperature overnight. 90 mL $Et_2O$ and 90 mL $H_2O$ are then added and the organic and aqueous phases are separated. The aqueous phase is washed with $Et_2O$ (6×60 mL) to remove the remaining traces of 4-bromoethylbenzoic acid. The aqueous phase is then reduced to ⅓ of its initial volume by evaporation of the water in a rotary evaporator (bath at 35° C.). 10 mL of hydrochloric acid (3M) is then added. The contents of the flask are then centrifuged. The supernatant is removed and the pellet is suspended in 15 mL of $Et_2O$ and centrifuged again. The operation is repeated 3 times and the pellets obtained are then solubilized in MeOH and evaporated to dryness on a rotary evaporator (35° C. bath) to obtain pure AG38 as a black flaky powder (336 mg, 0.28 mmol, 85%).

$^1$H NMR (DMSO, 500 MHz) δ (ppm): 8.30 (d; $^3$J=8.9 Hz; 4H); 8.12 (d; $^3$J=9.0 Hz; 4H); 7.95 (d; $^3$J=8.3 Hz; 4H); 7.43 (d; $^3$J=8.3 Hz; 4H); 7.28 (s; 2H); 7.08 (d; $^3$J=9.0 Hz; 4H); 6.88 (d; $^3$J=8.9 Hz; 4H); 4.24 (s; 4H); 3.96 (s; 4H); 3.74 (s; 6H); 3.08 (s; 12H); 2.76 (s; 12H).

Analytical HPLC (Gradient A): Tr=4.50 min.

AG22 (75 mg; 0.097 mmol, 1 eq) is dissolved in 60 mL dry THF in a 250 ml flask under argon. 4-bromoethylbenzoic acid (23 mg; 0.106 mmol, 1.1 eq) is then added and the mixture is left to stir under reflux overnight. After cooling, the supernatant is removed and the precipitate formed is washed with THF (3×15 mL), diethyl ether (2×15 mL) and pentane (2×15 mL). All the supernatants are combined and the solvents are removed under reduced pressure. The residue obtained is purified by silica gel chromatography column (8:2 Toluene/MeOH→100% MeOH) to isolate AG57 as a black flaky powder (20.7 mg, 0.021 mmol, 22%).

$^1$H NMR (DMSO, 500 MHz) δ (ppm): 8.36 (d; $^3$J=8.9 Hz; 4H); 8.07 (d; $^3$J=9.0 Hz; 4H); 7.98 (d; $^3$J=8.3 Hz; 2H); 7.24 (d; $^3$J=8.3 Hz; 2H); 7.00 (d; 3=9.0 Hz; 4H); 6.96 (s; 2H); 6.82 (d; $^3$J=8.9 Hz; 4H); 3.84 (s; 2H); 3.75 (s; 6H); 3.39 (s; 2H); 3.25 (s; 2H); 3.06 (s; 12H); 2.58 (s; 6); 2.24 (s; 6H)

Analytical HPLC (Gradient A): 4.48 min.

Compound AG46

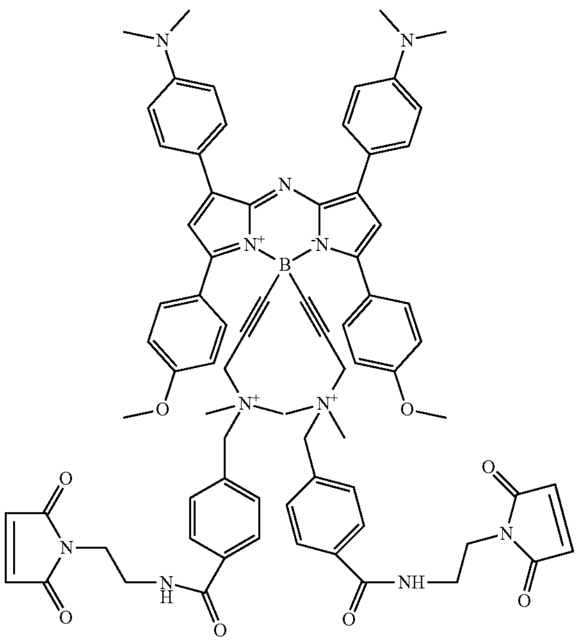

AG38 (250 mg, 0.209 mmol, 1 eq) is dissolved in 10 mL anhydrous DMF (dimethylformamide) in a 100 mL flask. HBTU (208 mg, 0.548 mmol, 2.6 eq) is dissolved in 10 mL anhydrous DMF before being added to the reaction mixture. 341 μL (1.959 mmol, 9.3 eq) of DIPEA (diisopropylethylamine) is then added and the mixture is left to stir at room temperature for 1 h. 109.2 mg (0.618 mmol, 2.9 eq) of 2-aminoethylmaleimide hydrochloride is dissolved in 10 mL of anhydrous DMF before being added to the reaction medium which is then stirred at room temperature overnight, evaporated to dryness and then purified by semi-preparative HPLC (25% ACN gradient→100% program 30 min) to isolate pure AG46 as a green solid (151 mg, 0.133 mmol, 63%).

$^1$H NMR (MeOD, 500 MHz) δ (ppm): 8.36 (d; $^3$J=8.9 Hz; 4H); 8.19 (d; $^3$J=8.9 Hz; 4H); 7.72 (d; 3=8.2 Hz; 4H); 7.39 (d; $^3$J=8.2 Hz; 4H); 7.22 (s; 2H); 7.18 (d; $^3$J=8.9 Hz; 4H); 7.09 (d; $^3$J=8.9 Hz; 4H); 6.76 (s; 4H); 4.18 (s; 4H); 3.87 (s; 4H); 3.76 (s; 6H); 3.71 (dd; $^3$J=6.3 Hz; $^3$J=4.6 Hz; 2H); 3.52 (dd; $^3$J=6.3 Hz; $^3$J=4.6 Hz; 2H); 3.20 (s; 12H); 2.84 (s; 12H)

$^{13}$C NMR (DMSO, 150 MHz): 171.1; 165.6; 160.9; 158.6; 158.3; 158.1; 157.8; 155.9; 151.0; 142.1; 141.6; 136.0; 134.6; 132.5; 132.0; 130.4; 130.1; 127.6; 124.3; 119.8; 116.7; 116.0; 114.7; 113.7; 112.1; 64.6; 55.4; 54.0; 49.1; 37.7; 37.1.

HR-MS (ESI) (Da): m/z calculated for $C_{76}H_{78}BN_{11}O_8^{2+}$ $[M]^{2+}$ 641.80585, found 641.80752.

HPLC-analytical (Gradient A): Tr=4.56 min.

Compound AG49

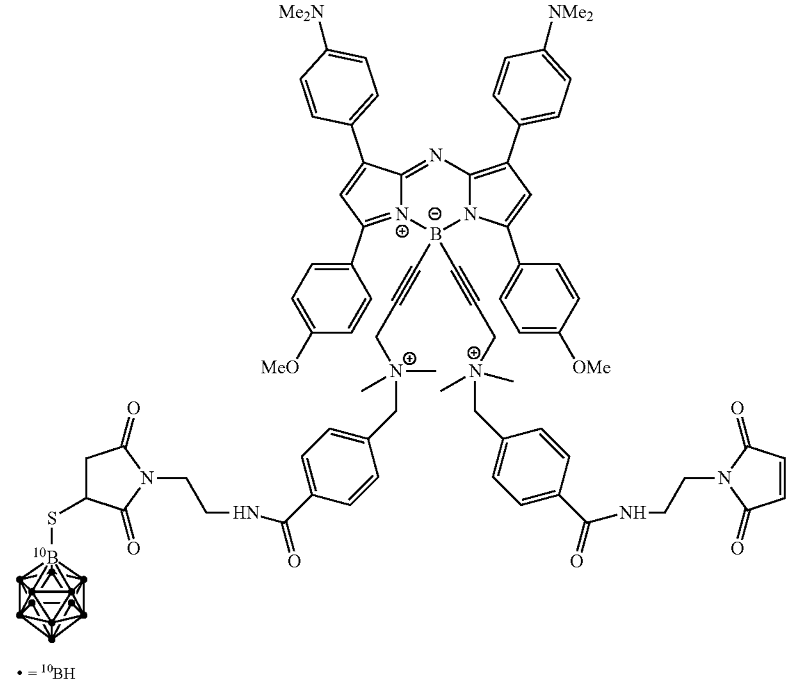

AG46 (120 mg; 79 μmol; 1 eq) is dissolved in 2 mL ACN (acetonitrile) in a 10 mL flask. 42 mg (166 μmol; 2.5 eq) of BSH is then added and the reaction is left to stir at 40° C. for 48 h. The reaction mixture is transferred to Falcons tubes and centrifuged. The supernatant is removed and the pellet is washed again with ACN (3×15 mL), DCM (1×15 mL), $Et_2O$ (2× 15 mL) and pentane (2×15 mL), isolating AG49 as a blue precipitate (62 mg, 41.9 μmol, 53%).

$^1$H NMR (DMSO, 500 MHz) δ (ppm): 8.65-8.63 (m; 1H); 8.48-8.42 (m; 1H); 8.33-8.30 (m; 4H); 8.13-8.11 (m; 4H); 7.82-7.75 (m; 4H); 7.39-7.36 (m; 4H); 7.28-7.27 (m; 2H); 7.09-7.07 (m; 4H); 7.00-6.99 (m; 1H); 6.89-6.85 (m; 4H); 4.17 (t; $^3$J=17.9 Hz; 4H); 3.97-3.90 (m; 4H); 3.74-3.73 (m; 6H); 3.62 (dd; $^3$J=8.0 Hz; 4J=3.1 Hz; 2H); 3.59-3.55 (m; 2H); 3.54-3.48 (m; 4H); 3.07 (s; 12H); 3.03 (d; $^3$J=8.5 Hz; 1H); 2.99 (d; $^3$J=8.5 Hz; 1H); 2.78-2.73 (m; 13H); 1.03 (bs; 11H).

HR-MS (ESI) (Da): m/z calculated for $C_{76}H_{90}B^{10}B_{12}N_{11}Na^{2+}O_8S^{2+}$ $[M+2Na]^{2+}$ 746.90622, found 746.90811.

HPLC-analytical (Gradient A): Tr=5.32 min.

Compound AG58

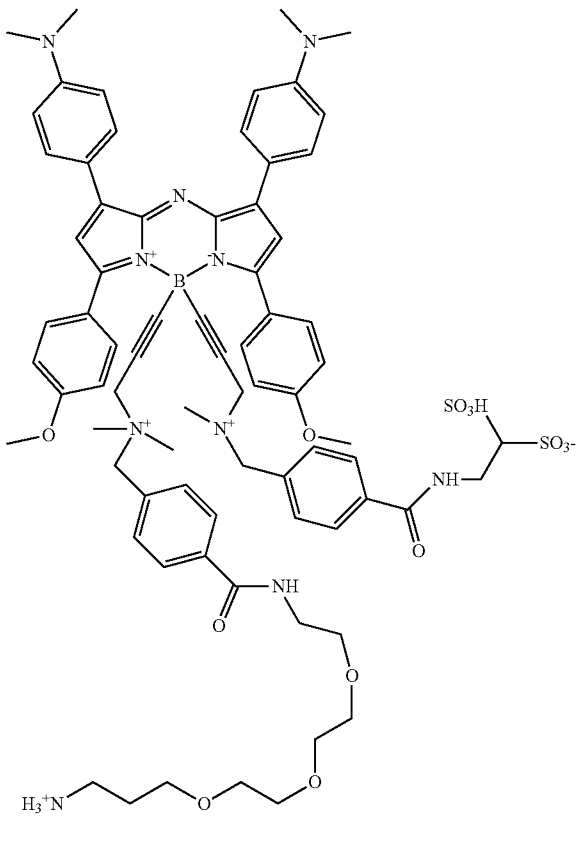

AG35-3 (35 mg; 0.029 mmol; 1 eq) is dissolved in 3 mL DMF in a 50 mL flask. 25 mg HBTU (2-(1H-benzotriazol-1-yl)-1,1,3,3-tetramethyluronium hexafluorophosphate, Hexafluorophosphate Benzotriazole Tetramethyl Uronium) (0.067 mmol; 2.3 eq) dissolved in 3 mL DMF is then introduced, followed by 40 μL DIPEA (0.232 mmol, 8 eq). The reaction was stirred at room temperature for 30 min under argon. A 0.5M solution of $H_2N\text{-}CH_2\text{—}CH\text{-}(SO_3^-)_2$ (TBA or tetrabutylammonium salt) (61 μL, 0.030 mmol, 1.1 eq) in 3 mL DMF is added to the reaction medium, which is then stirred at room temperature for 1 h. 14 mg (0.030 mmol, 1.1 eq) of TOTA-Boc in 3 mL DMF is then added to the solution, which is further stirred for 1 h at room temperature. The reaction mixture is evaporated to dryness, solubilised in 30 mL ACN, then 15 mL HCl (3M) is added. The reaction is stirred at 40° C. for 2 h. The reaction crude is evaporated to dryness and purified by semi-preparative HPLC (gradient 25%>100%, program 40 min), freeze-dried, giving pure AG58 as a green powder (7 mg, 5 μmol, 18%).

$^1$H NMR (DMSO, 500 MHz) δ (ppm): 8.69 (t; $^3$J=4.4 Hz; 1H); 8.50 (t; $^3$J=5.5 Hz; 1H); 8.23 (d; $^3$J=8.9 Hz; 4H); 8.12 (d; $^3$J=9.0 Hz; 4H); 7.94 (d; $^3$J=8.3 Hz; 2H); 7.90 (d; $^3$J=8.3 Hz; 2H); 7.63 (d; $^3$J=8.3 Hz; 2H); 7.60 (bs; 3H); 7.56 (d; $^3$J=8.3 Hz; 2H); 7.18 (s; 2H); 6.98 (d; $^3$J=8.9 Hz; 4H); 6.87 (d; $^3$J=8.9 Hz; 4H); 4.60 (s; 2H); 4.28 (s; 2H); 3.95 (t; $^3$J=4.4 Hz; 2H); 3.80 (s; 2H); 3.72 (t; $^3$J=4.9 Hz; 1H); 3.63 (s; 6H); 3.51-3.41 (m; 12H); 3.33 (dd; $^3$J=12.4 Hz; $^3$J=6.6 Hz; 4H); 3.07 (s; 12H); 3.06-3.01 (m; 4H); 2.85-2.82 (m; 2H); 2.72 (s; 6H); 1.79-1.73 (m; 4H); 1.60-1.55 (m; 2H).

HR-MS (ESI) (Da): m/z calculated for $C_{76}H_{93}BN_{10}O_{13}S_2^{2+}$ $[M]^{2+}$ 714.32235, found 714.32560.

HPLC-analytical (Gradient A): Tr=4.32 min.

Compound AG60

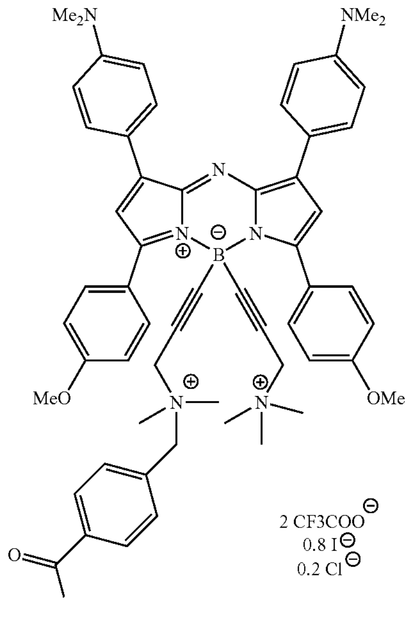

-continued

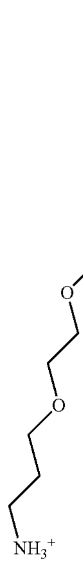

AG57-3 (21 mg; 0.021 mmol; 1 eq) is dissolved in 2 mL DMF. 20 mg (0.052 mmol; 2.5 eq) of HBTU is dissolved in 2 mL before being added to the AG57-3 solution, followed by 32 μL (0.160 mmol; 8.6 eq) of DIPEA. The reaction mixture was stirred at 30° C. under argon. After 30 min, 10 mg (0.024 mmol; 1.1 eq) of TOTA-Boc were added and the solution was stirred for 1.5 hours at 30° C. The solvents are removed under reduced pressure and the resulting residue is purified by silica gel chromatography column (eluent: 100% DCM→50/50 DCM/MeOH), allowing the TOTA intermediate to be isolated as a black solid.

Then, in a 25 mL flask under argon, the previous intermediate is dissolved in 4 mL of dry DCM. Iodomethane (1 mL, large excess) is added and the reaction is stirred at room temperature for 1 h. The solvents are removed under reduced pressure and the resulting residue is solubilised in 20 mL ACN. 10 ml of an aqueous HCl (3M) solution is added and the reaction is left to stir at 40° C. for 2 h. The reaction medium is evaporated to dryness and purified by semi-preparative HPLC (20% ACN gradient→100% in 30 min), then lyophilized overnight to isolate pure AG60 as a blue solid (4 mg, 2.4 μmol, 14%).

$^{1}H$ NMR (ACN, 500 MHz) δ (ppm): 8.21-8.19 (m; 2H); 8.18-8.15 (m; 2H); 8.11-8.08 (m; 4H); 7.89 (t; $^{3}J$=8.6 Hz; 2H); 7.86 (s; 1H); 7.52 (bs; 3H); 7.36 (d; $^{3}J$=8.0 Hz; 1H); 7.32 (d; $^{3}J$=8.1 Hz; 1H); 7.04-7.01 (m; 4H); 7.00 (d; $^{3}J$=8.7 Hz; 2H); 6.89-6.86 (m; 4H); 4.01 (s; 1H); 3.86 (s; 1H); 3.85 (s; 1H); 3.81 (s; 1H); 3.80 (s; 3H); 3.76 (s; 3H); 3.66 (q; J=5.5 Hz; 2H); 3.60-3.58 (m; 4H); 3.57-3.55 (m; 6H); 3.53 (t; $^{3}J$=5.8 Hz; 2H); 3.44 (quin; $^{3}J$=6.4 Hz; 3H) 3.35 (s; 1H); 3.08 (s; 12H); 2.83 (s; 5H); 2.70 (s; 3H); 2.66 (s; 3H); 2.60 (s; 3H); 1.90-1.85 (m; 3H); 1.83-1.78 (m; 2H).

HR-MS (ESI) (Da): m/z calculated for $C_{67}H_{85}BN_9O_6^{3+}$ $[M]^{3+}$ 374.22331, found 374.22292.

HPLC-analytical (Gradient A): Tr=4.18 min.

Compound AG47

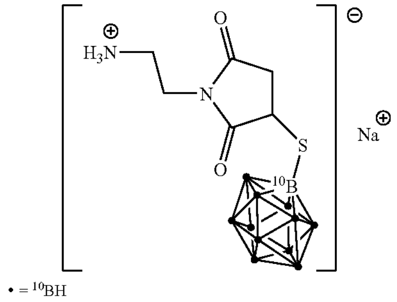

In a 10 mL flask, 2-aminoethylmaleimide hydrochloride (10.3 mg; 58 μmol; 1 eq) is dissolved in 2 mL of ACN. 10B-BSH (12.3 mg; 58 μmol; 1 eq) is then added and the reaction is left to stir at room temperature for 1 h. The reaction crude is evaporated to dryness to isolate AG47 as a white solid (23 mg; 58 μmol; 1 eq).

Compound AG66

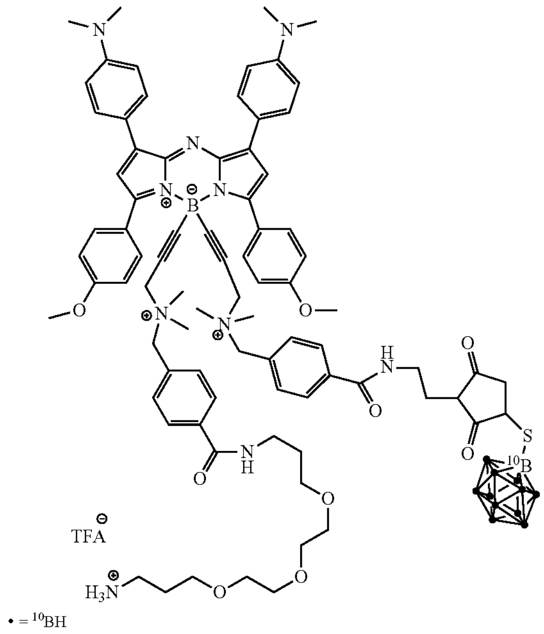

In a 100 mL flask, AG38 (200 mg; 178 μmol; 1 eq) is solubilized in 16 mL DMF. HBTU (158 mg; 406 μmol; 2.3 eq) is dissolved in 16 mL before being added to the reaction followed by DIPEA (248 μL; 800 μmol; 8 eq). The reaction was left to stir at room temperature for 30 min under argon. AG47 (72 mg; 186 μmol; 1.05 eq) is dissolved in 16 mL DMF and added to the reaction medium. The reaction is left to stir at room temperature for 1 h. TOTA-Boc (78 mg; 186 μmol; 1.05 eq) is dissolved in 16 mL DMF before being added. After 1 h the contents of the flask are transferred to a separating funnel and 100 mL DCM and 50 mL $H_2O$ are added. The two phases are separated, the aqueous phase is extracted with DCM (3× 50 mL). The organic phases are combined, washed with brine (1×100 mL) and evaporated to dryness. The crude obtained is solubilized in 40 mL ACN and 15 mL HCl (3M) is added. The mixture is left to stir for 2 h at 40° C. and the crude is evaporated to dryness before being purified by semi-preparative HPLC (gradient A). The resulting product was run on C1-ion exchange resin (IRA 410) to isolate AG66 as a green precipitate (33 mg; 21 μmol; 12%). $^{1}H$ NMR (ACN-$d_3$/$D_2O$, 600 MHz, 343 K) δ (ppm): 8.19 (d, $^{3}J$=8.2 Hz; 4H); 8.07 (d $^{3}J$=8.3 Hz, 4H); 7.68-7.64 (m, 4H); 7.35-7.22 (m; 10H); 7.11 (s, 2H); 7.01-6.99 (m, 4H); 4.10 (s; 2H); 3.95 (s; 2H); 3.78 (s, 2H); 3.65-3.63 (m, 8H), 3.55-3.52 (m, 12H); 3.50-3.48 (m, 3H); 3.42-3.38 (m, 2H), 3.35-3.32 (m, 2H), 3.04-3.02 (m, 2H); 2.99-2.96 (m, 1H); 2.92-2.88 (m, 1H); 2.74 (s, 6H); 2.66 (s, 6H), 1.85 (p, $^{3}J$=5.9 Hz, 2H); 1.80-1.76 (m, 2H); 1.21 (bs; 11H)

$^{13}C$ NMR (ACN-$d_3$/$D_2O$, 125 MHz, 343 K) δ (ppm): 28.1; 30.3; 30.4; 38.9; 39.4; 39.8; 41.1; 41.1; 43.3; 43.4; 45.3; 51.7; 56.4; 56.6; 57.4; 67.4 67.5; 70.1; 70.3; 71.1; 71.2; 71.2; 71.2; 71.3; 71.4; 88.2; 115.9; 119.1; 125.8; 129.4; 129.6; 129.6; 129.9; 131.3; 131.4; 132.5; 132.6; 134.1; 134.3; 134.4; 137.7; 138.1; 138.2; 142.3; 144.5; 147.9; 159.2; 163.3; 169.6; 169.6; 180.4; 181.9.

$^{11}B$ NMR (ACN-$d_3$/$D_2O$, 193 MHz, 343 K): −9.39 (bs, aza-BODIPY); −14.59 (bs, BSH); −16.20 (s, BSH); −19.10 (bs, BSH)

$^{10}B$ NMR (ACN-$d_3$/$D_2O$, 64 MHz, 343 K): −9.08 (bs, aza-BODIPY); −16.27 (s, BSH); −17.28 (s, BSH).

HR-MS (ESI) (Da): m/z calculated for $C_{80}H_{107}{}^{11}B^{10}B_{12}N_{11}O_9S^+$ $[M]^+$ 1528.96140, found 1528.96362.

HPLC-analytical (Gradient A): Tr=4.53 min.

Example 2: Small Animal Fluorescence Imaging Procedure

Five-week-old female NMRI Nu/Nu mice are caged in groups of 5, with food and water at libitum, and day/night lighting from 12:00 to 12:00, according to current ethical recommendations.

At the age of 6 weeks, U87MG tumor cells (3 million/100 μL) were injected subcutaneously into the right lower limb: the animals were sedated by gas anaesthesia during this injection. The animals are placed back in the cage for the duration of the tumor development, that means approximately 3 weeks.

When the tumor reaches approximately 100 $mm^3$ or more, the solution containing the AG22 compound is injected intravenously (25 to 50 μg/mouse), in the tail vein of the animal placed under gas anaesthesia. The animal is then awakened during the external imaging phases. For each imaging session, the animal is placed under gas anaesthesia, the imaging is performed and then the animal is returned to its cage.

Imaging is performed with an excitation at 830 nm and then the fluorescence signal is collected using a long pass filter between 1064 and 1700 nm.

We observe (FIG. 1) the mouse with a U87MG tumour in the right hind leg before and 24 hours after injection of the AG22 compound. The upper planes are recorded with NIR imaging. Fluo800 corresponds to excitation at 780 nm and collection between 830 and 900 nm. The lower planes are excited at 830 nm (SWIR800) and the emission is collected using a 1064 nm long pass filter.

The experiment is repeated with the compound AG66.

We observe the mouse with a U87MG tumour on the right hind leg, respectively from left to right: before, at 5 h and at 48 h after injection of the AG66 compound.

The compounds according to the invention can thus be observed in the wavelength range from 1000 to 1700 nm: these wavelengths facilitate in-depth detection with better resolution.

The compounds according to the invention also allow the delivery of small compounds, such as boron complexes.

LIST OF REFERENCES

[1] Bruns et al, Nat Biomed Eng. 2017; doi: 10.1038/s41551-017-0056/Carr et al, Proc Natl Acad Sci USA. 2018 115 (17): 4465-70/Thimsen et al, Nanophotonics 2017; 6 (5): 1043-1054).

[2] PAC, 1996, 68, 2193 (Basic terminology of stereochemistry (IUPAC Recommendations 1996)) page 2205.

[3] Gravier et al, Mol Pharm. 2014; doi: 10.1021/mp500329z., page 3134.

[4] Hirsjärvi et al, Nanomedicine. 2013; doi: 10.1016/j.nano.2012.08.005, page 376.

[5] Garcia et al, Biomater Sci. 2018; doi: 10.1039/c8bm00396c, page 1755.

[6] Reagan-Shaw et al, FASEB J, 2007, Vol 22 page 660, doi: 10.1096/fj.07-9574LSF

The invention claimed is:

1. A method for optical imaging comprising, injecting in a medium to be observed a fluorophore compound of formula I Formula I

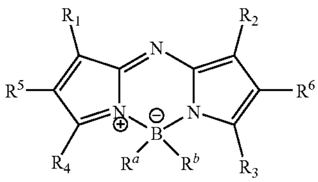

$R^1$, $R^2$, $R^3$ and $R^4$, identical or different, represent a C5-C7 aryl or heteroaryl group, optionally substituted with at least one group chosen from halogen, —$NR^cR^d$, —$OR^d$, hydrazine, —$CF_3$ and —CN, at least one of $R^1$ or $R^2$ represents a C5-C7 aryl or heteroaryl group substituted by a —$NR^cR^d$ group, $R^5$ and $R^6$, identical or different, represent a hydrogen, a halogen, a C1-C15 group comprising an aldehyde, ketone, carboxlic acid or ester function, a nitrile, —$SO_3Na$, a vinyl group optionally substituted by a ketone, ester or aromatic group, an imine substituted by an alkyl or aromatic group, an alkyne group optionally substituted by an alkyl or aromatic group, SPh, an aromatic chalcogen, an amide, a C5-C7 aryl or heteroaryl group, optionally substituted by at least one group chosen from a halogen, —$NR^cR^d$, —$OR^d$, hydrazine, —$CF_3$ and —CN, optionally $R^3$ and $R^5$ and/or $R^4$ and $R^6$ are covalently bonded and together form a C5-C7 aryl or heteroaryl group, optionally substituted by at least one group chosen from halogen, —$NR^cR^d$, —$OR^d$, hydrazine, —$CF_3$ and —CN, $R^c$ and $R^d$, identical or different, represent hydrogen or a linear or branched C1-C3 alkyl chain, $R^a$ and $R^b$, identical or different, represent:

a halogen, a C1-C50, aliphatic or heteroaliphatic, linear or branched, saturated or unsaturated group, optionally comprising one or more aromatic or heteroaromatic groups, optionally comprising one or more heteroatoms chosen from O, N, P and/or S, a biological vector covalently coupled via a C1-C50, aliphatic or heteroaliphatic, linear or branched, saturated or unsaturated group, optionally comprising one or more aromatic or heteroaromatic groups, optionally comprising one or more heteroatoms chosen from O, N, P and/or S, a metal complex, formed by a chelating agent and a metal, a radiometallic complex, formed by a chelating agent and a radiometal, or a cyclic or linear peptide, an antibody, an antibody fragment, a nanobody, an affibody, an aptamer, a short DNA or RNA sequence, a sugar, a polysaccharide, an amino acid, a vitamin, a AMD3100 type molecule, a PSMA ligand, a steroid, a fatty acid, a polyamine, a polyphenol, a DNA base or caffeine;

detecting the fluorescence signal of the injected fluorophore in the optical window ranging from 1000 to 1700 nm.

2. The method according to claim 1, wherein $R_5$ and $R_6$ are a hydrogen.

3. The method according to claim 1, wherein $R_1$ and $R_2$, identical or different, represent a C5-C7 aryl group substituted by a —$NR^cR^d$ group and further substituted with a group chosen from halogen, —$OR^d$, hydrazine, —$CF_3$ and —CN.

4. The method according to claim 1, wherein $R_1$ and/or $R_2$ represent a phenyl group substituted by a —$NR^cR^d$ group.

5. The method according to claim 1, wherein $R^a$ and $R^b$, identical or different, are chosen from a group selected from halogen, hydrophilic group, group comprising a bioconjugable function, —$NH_2$, —$Si(OMe)_3$, group comprising a biological vector, $PPh_2$-Au(I), $PPh_2$-Pt(II), $PPh_2$-Pt(IV), phenylpyridine-Au(III), DOTA-In(III), DOTAGA-In(III), NODAGA-Cu(II), NODAGA-Ga(III), αvβ3 integrin-targeting c(RGDfK) (SEQ ID NO: 1), neuropilin-targeting ATWLPPR (SEQ ID NO: 2), anti-CD44, a thioglucose, a peracetylated thioglucose, folic acid, a AMD3100-type ligand, a PSMA ligand, spermine, spermidine, cadaverine, putrescine, resveratrol, a DNA base, caffeine or progesterone; the hydrophilic group is selected from groups of the following formulae:

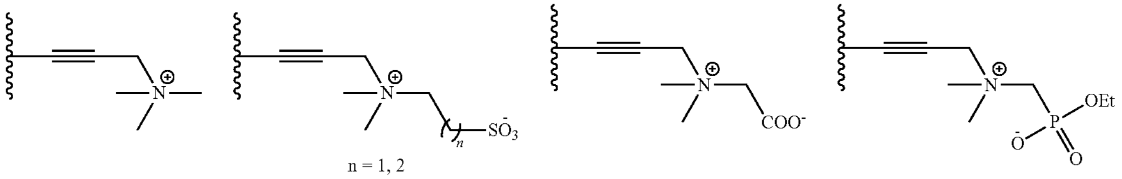

n = 1, 2

-continued
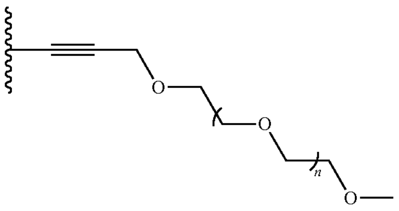
n = 1 to 10
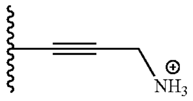
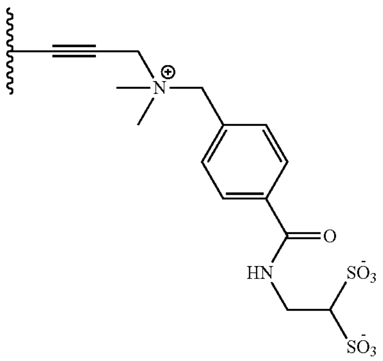
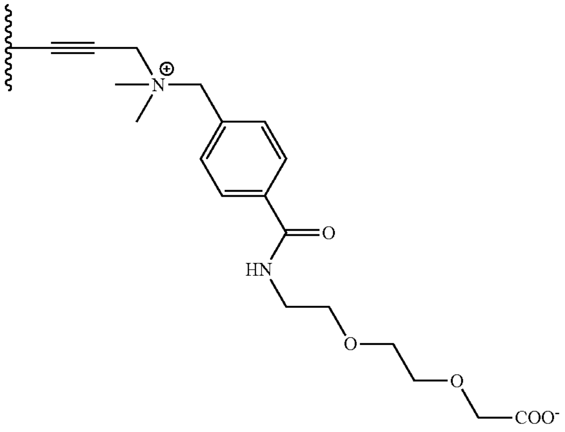
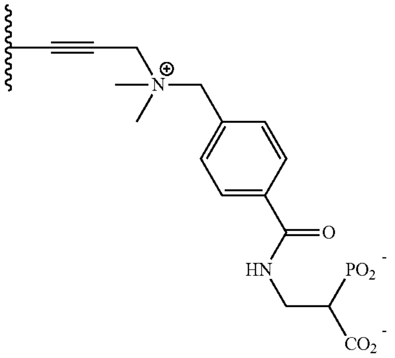
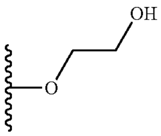
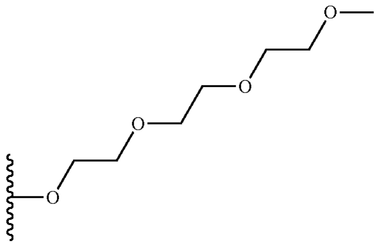
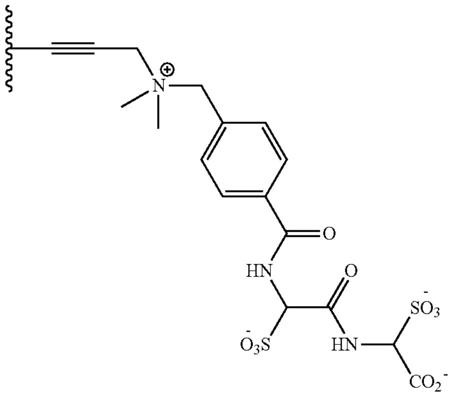
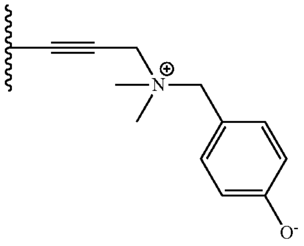
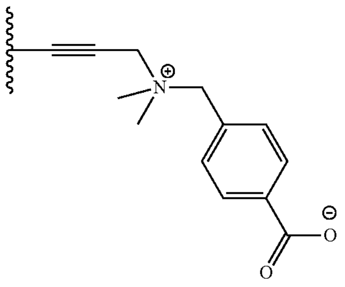
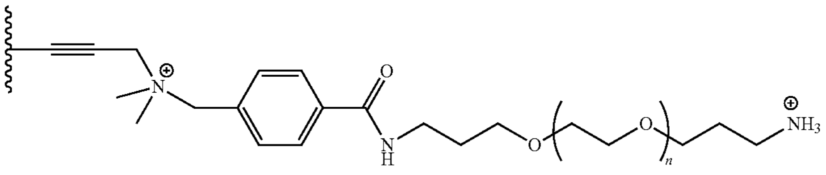
n = 1 to 12 wherein the group comprising a bioconjugable function is selected from the group of the following formulae:

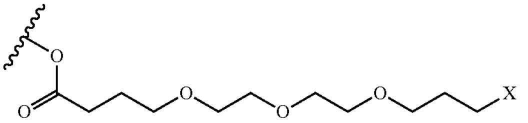

or

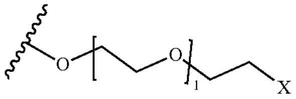

or

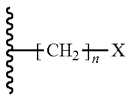

n = 1 to 12 wherein X is selected from the group consisting of:

$NH_2$ $N_3$

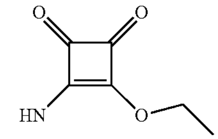

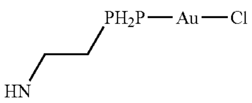

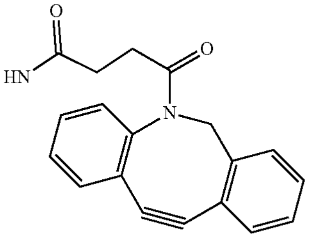

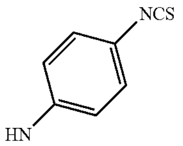

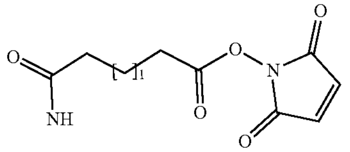

n = 1 to 4

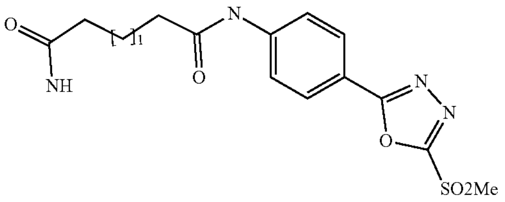

n = 1 to 4

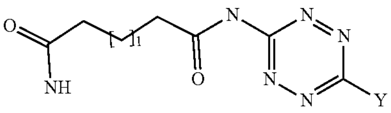

n = 1 to 4
Y is H, Cl or Me

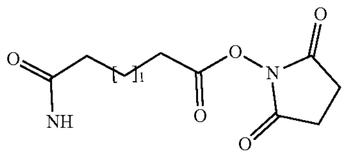

n = 1 to 4

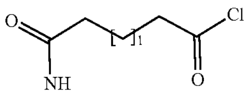

n = 1 to 4

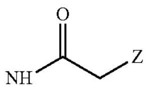

Z is Br, Cl or I and

-continued

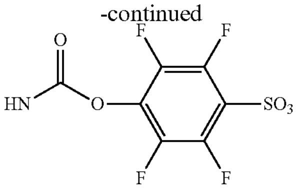

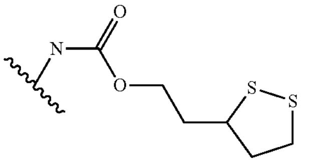

or

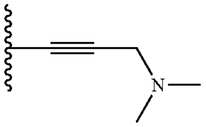

or

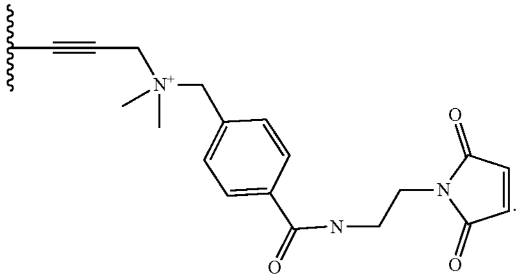

6. The method according to claim 1, wherein the fluorophore compound is chosen from fluorophore compounds of formula II:

Formula II

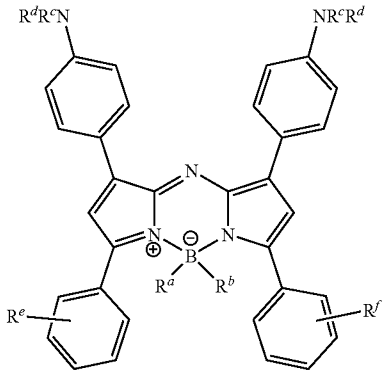

wherein, $R^a$ and $R^b$, identical or different, represent:

a halogen a C1-C50, aliphatic or heteroaliphatic, linear or branched, saturated or unsaturated group, optionally comprising one or more aromatic or heteroaromatic groups, optionally comprising one or more heteroatoms chosen from O, N, P and/or S, a biological vector covalently coupled via a C1-C50, aliphatic or heteroaliphatic, linear or branched, saturated or unsaturated group, optionally comprising one or more aromatic or heteroaromatic groups, optionally comprising one or more heteroatoms chosen from O, N, P and/or S, a metal complex, formed by a chelating agent and a metal, a radiometallic complex, formed by a chelating agent and a radiometal, or acyclic or linear peptide, an antibody, an antibody fragment, a nanobody, an affibody, an aptamer, a short DNA or RNA sequence, a sugar, a polysaccharide, an amino acid, a vitamin, a AMD3100 type molecule, a PSMA ligand, a steroid, a fatty acid, a polyamine, a polyphenol, a DNA base or caffeine;

$R^c$ and $R^d$, identical or different represent hydrogen or a linear or branched C1-C3 alkyl chain, $R^e$ and $R^f$, identical or different, are independently selected from a hydrogen, a halogen, —$NR^cR^d$, $OR^d$, hydrazine, —$CF_3$ or —CN.

7. The method according to claim 1, wherein $R^c$ and $R^d$ are —$CH_3$.

8. A composition comprising a fluorophore compound of formula I according to claim 1, and a pharmaceutically acceptable excipient and/or a solvent.

9. The composition according to claim 8, wherein the composition has a pH in the range from 4 to 10.

10. The method according to claim 1, wherein the fluorophore compound is encapsulated.

11. A method for in vitro identification of a biological target, comprising:

adding to a sample comprising the biological target a fluorophore compound of formula I, Formula I

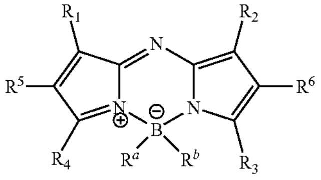

$R^1$, $R^2$, $R^3$ and $R^4$, identical or different, represent a C5-C7 aryl or heteroaryl group, optionally substituted with at least one group chosen from halogen, —$NR^cR^d$, —$OR^d$, hydrazine, —$CF_3$ and —CN, at least one of $R_1$ or $R_2$ represents a C5-C7 aryl or heteroaryl group substituted by a —$NR^cR^d$ group, $R_5$ and $R_6$, identical or different, represent a hydrogen, a halogen, a C1-C15 group comprising an aldehyde, ketone, carboxylic acid or ester function, a nitrile, —$SO_3Na$, a vinyl group optionally substituted by a ketone, ester or aromatic group, an imine substituted by an alkyl or aromatic group, an alkyne group optionally substituted by an alkyl or aromatic group, SPh, an aromatic chalcogen, an amide, a C5-C7 aryl or heteroaryl group, optionally substituted by at least one group chosen from a halogen, —$NR^cR^d$, —$OR^d$, hydrazine, —$CF_3$ and —CN, optionally $R^3$ and $R^5$ and/or $R^4$ and $R^6$ are covalently bonded and together form a C5-C7 aryl or heteroaryl group, optionally substituted by at least one group chosen from halogen, —$NR^cR^d$, —$OR^d$, hydrazine, —$CF_3$ and —CN, $R^c$ and $R^d$, identical or different, represent hydrogen or a linear or branched C1-C3 alkyl chain, $R^a$ and $R^b$, identical or different, represent:

a halogen a C1-C50, aliphatic or heteroaliphatic, linear or branched, saturated or unsaturated group, optionally comprising one or more aromatic or heteroaromatic groups, optionally comprising one or more heteroatoms chosen from O, N, P and/or S, a biological vector covalently coupled via a C1-C50, aliphatic or heteroaliphatic, linear or branched, saturated or unsaturated group, optionally comprising one or more aromatic or heteroaromatic groups, optionally comprising one or more heteroatoms chosen from O, N, P and/or S, a metal complex, formed by a chelating agent and a metal, a radiometallic complex, formed by a chelating agent and a radiometal, or a cyclic or linear peptide, an antibody, an antibody fragment, a nanobody, an affibody, an aptamer, a short DNA or RNA sequence, a sugar, a polysaccharide, an amino acid, a vitamin, a AMD3100 type molecule, a PSMA ligand, a steroid, a fatty acid, a polyamine, a polyphenol, a DNA base or caffeine;

collecting a fluorescence signal in the optical window from 1000 to 1700 nm, and obtaining an image or a signal to identify biological targets via fluorescence.

12. The method according to claim 4, wherein the —$NR^cR^d$ group is in the para position.

13. The method according to claim 6, wherein the fluorophore compound is chosen from compounds of formula II wherein $R^e$ and $R^d$ are —$CH_3$.

14. The composition according to claim 8, wherein the composition has a pH in the range from 6 to 8.

15. The method according to claim 11, wherein the fluorescence signal is collected via microscopy, flow cytometry, optical imaging by fluorescence reflection (2D or 3D), or optical probe.

16. A composition comprising the fluorophore compound according to claim 6, and a pharmaceutically acceptable excipient and/or a solvent.

17. The method according to claim 11, wherein the fluorophore compound is chosen from fluorophore compounds of formula II:

Formula II

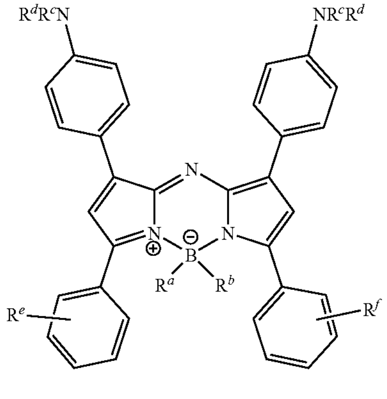

wherein, $R^a$ and $R^b$, identical or different, represent:

a halogen a C1-C50, aliphatic or heteroaliphatic, linear or branched, saturated or unsaturated group, optionally comprising one or more aromatic or heteroaromatic groups, optionally comprising one or more heteroatoms chosen from O, N, P and/or S, a biological vector covalently coupled via a C1-C50, aliphatic or heteroaliphatic, linear or branched, saturated or unsaturated group, optionally comprising one or more aromatic or heteroaromatic groups, optionally comprising one or more heteroatoms chosen from O, N, P and/or S, a metal complex, formed by a chelating agent and a metal, a radiometallic complex, formed by a chelating agent and a radiometal, or a cyclic or linear peptide, an antibody, an antibody fragment, a nanobody, an affibody, an aptamer, a short DNA or RNA sequence, a sugar, a polysaccharide, an amino acid, a vitamin, a AMD3100 type molecule, a PSMA ligand, a steroid, a fatty acid, a polyamine, a polyphenol, a DNA base or caffeine;

$R^e$ and $R^d$, identical or different, represent hydrogen or a linear or branched C1-C3 alkyl chain, $R^e$ and $R^f$, identical or different, are independently selected from a hydrogen, a halogen, —$NR^cR^d$, $OR^d$, hydrazine, —$CF_3$ or —CN.

18. A method for in vivo identification of a biological target comprising:

injecting or spraying to a person or an animal, in need thereof a composition comprising a fluorophore compound of formula I, Formula I

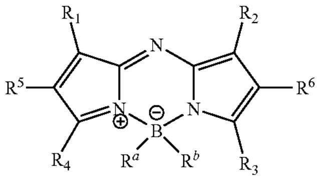

$R_1$, $R_2$, $R_3$ and $R_4$, identical or different, represent a C5-C7 aryl or heteroaryl group, optionally substituted with at least one group chosen from halogen, —$NR^cR^d$, —$OR^d$, hydrazine, —$CF_3$ and —CN, at least one of $R^1$ or $R^2$ represents a C5-C7 aryl or heteroaryl group substituted by a —$NR^cR^d$ group, $R_5$ and $R_6$, identical or different, represent a hydrogen, a halogen, a C1-C15 group comprising an aldehyde, ketone, carboxylic acid or ester function, a nitrile, —$SO_3Na$, a vinyl group optionally substituted by a ketone, ester or aromatic group, an imine substituted by an alkyl or aromatic group, an alkyne group optionally substituted by an alkyl or aromatic group, SPh, an aromatic chalcogen, an amide, a C5-C7 aryl or heteroaryl group, optionally substituted by at least one group chosen from a halogen, —$NR^cR^d$, —$OR^d$, hydrazine, —$CF_3$ and —CN, optionally $R^3$ and $R^5$ and/or $R^4$ and $R^6$ are covalently bonded and together form a C5-C7 aryl or heteroaryl group, optionally substituted by at least one group chosen from halogen, —$NR^cR^d$, —$OR^d$, hydrazine, —$CF_3$ and —CN, $R^c$ and $R^d$, identical or different, represent hydrogen or a linear or branched C1-C3 alkyl chain, $R^a$ and $R^b$, identical or different, represent:

a halogen a C1-C50, aliphatic or heteroaliphatic, linear or branched, saturated or unsaturated group, optionally comprising one or more aromatic or heteroaromatic groups, optionally comprising one or more heteroatoms chosen from O, N, P and/or S, a biological vector covalently coupled via a C1-C50, aliphatic or heteroaliphatic, linear or branched, saturated or unsaturated group, optionally comprising one or more aromatic or heteroaromatic groups, optionally comprising one or more heteroatoms chosen from O, N, P and/or S, a metal complex, formed by a chelating agent and a metal, a radiometallic complex, formed by a chelating agent and a radiometal, or a cyclic or linear peptide, an antibody, an antibody fragment, a nanobody, an affibody, an aptamer, a short DNA or RNA sequence, a sugar, a polysaccharide, an amino acid, a vitamin, a AMD3100 type molecule, a PSMA ligand, a steroid, a fatty acid, a polyamine, a polyphenol, a DNA base or caffeine;

collecting a fluorescence signal in the optical window from 1000 to 1700 nm, obtaining an image or a signal to visualize or identify the biological target, if present, via fluorescence.

19. The method according to claim 18, wherein the fluorophore compound is chosen from fluorophore compounds of formula II:

Formula II

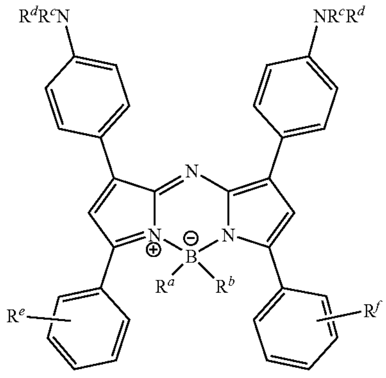

wherein, $R^a$ and $R^b$, identical or different, represent:

a halogen a C1-C50, aliphatic or heteroaliphatic, linear or branched, saturated or unsaturated group, optionally comprising one or more aromatic or heteroaromatic groups, optionally comprising one or more heteroatoms chosen from O, N, P and/or S, a biological vector covalently coupled via a C1-C50, aliphatic or heteroaliphatic, linear or branched, saturated or unsaturated group, optionally comprising one or more aromatic or heteroaromatic groups, optionally comprising one or more heteroatoms chosen from O, N, P and/or S, a metal complex, formed by a chelating agent and a metal, a radiometallic complex, formed by a chelating agent and a radiometal, or a cyclic or linear peptide, an antibody, an antibody fragment, a nano body, an affibody, an aptamer, a short DNA or RNA sequence, a sugar, a polysaccharide, an amino acid, a vitamin, a AMD3100 type molecule, a PSMA ligand, a steroid, a fatty acid, a polyamine, a polyphenol, a DNA base or caffeine;

$R^c$ and $R^d$, identical or different, represent hydrogen or a linear or branched C1-C3 alkyl chain, $R^e$ and $R^f$, identical or different, are independently selected from a hydrogen, a halogen, —$NR^cR^d$, OR, hydrazine, —$CF_3$ or —CN.

* * * * *